US012465368B2

(12) United States Patent
Miao

(10) Patent No.: US 12,465,368 B2
(45) Date of Patent: Nov. 11, 2025

(54) HEMOSTATIC CLIP ASSEMBLY AND TWO-PIECE FORCEPS

(71) Applicant: JIANGSU VEDKANG MEDICAL SCIENCE AND TECHNOLOGY CO., LTD., Jiangsu (CN)

(72) Inventor: Donglin Miao, Changzhou (CN)

(73) Assignee: JIANGSU VEDKANG MEDICAL SCIENCE AND TECHNOLOGY CO., LTD., Changzhou (CN)

( * ) Notice: Subject to any disclaimer, the term of this patent is extended or adjusted under 35 U.S.C. 154(b) by 0 days.

(21) Appl. No.: 19/058,000

(22) Filed: Feb. 20, 2025

(65) Prior Publication Data

US 2025/0186054 A1 Jun. 12, 2025

Related U.S. Application Data

(63) Continuation-in-part of application No. PCT/CN2024/080849, filed on Mar. 8, 2024.

(30) Foreign Application Priority Data

Mar. 10, 2023 (CN) ......................... 202310225453.3
Mar. 10, 2023 (CN) ......................... 202320441753.0

(51) Int. Cl.
*A61B 17/122* (2006.01)
*A61B 17/00* (2006.01)
*A61B 17/12* (2006.01)

(52) U.S. Cl.
CPC .. *A61B 17/122* (2013.01); *A61B 2017/00367* (2013.01); *A61B 2017/00477* (2013.01); *A61B 2017/12004* (2013.01)

(58) Field of Classification Search
CPC ..... A61B 17/122; A61B 17/10; A61B 17/083; A61B 2017/00367; A61B 2017/00477; A61B 2017/12004
See application file for complete search history.

(56) References Cited

U.S. PATENT DOCUMENTS

2005/0070758 A1 3/2005 Wells et al.
2008/0046002 A1 2/2008 Renger et al.
(Continued)

FOREIGN PATENT DOCUMENTS

CN 204671214 U 9/2015
CN 108013914 A 5/2018
(Continued)

OTHER PUBLICATIONS

International Search Report in PCT/CN2024/080849 mailed on Jun. 12, 2024, 7 pages.

(Continued)

*Primary Examiner* — Brooke Labranche
(74) *Attorney, Agent, or Firm* — PORUS IP LLC

(57) ABSTRACT

Disclosed is a hemostatic clip assembly. The hemostatic clip assembly comprises a sleeve, the two-piece forceps, and a pulling device connected with the two-piece forceps. The two-piece forceps and the pulling device are at least partially located within the sleeve. The two-piece forceps include a fixing member and two clip pieces each of which includes a first clip section and a second clip section. The fixing member is provided through the second clip section. The second clip section is provided with a first locking mechanism and a second locking mechanism. An end of the pulling device is detachably connected with the two-piece forceps. The sleeve is provided with a third locking mechanism. The two-piece forceps move toward a proximal end under an action of the pulling device when the pulling device is disconnected from the second locking mechanisms. The pulling device includes a rod portion and a connection portion.

19 Claims, 26 Drawing Sheets

(56) References Cited

U.S. PATENT DOCUMENTS

| | | | |
|---|---|---|---|
| 2013/0023911 | A1 | 1/2013 | Esanu |
| 2014/0171974 | A1 | 6/2014 | Zhu |
| 2018/0078258 | A1 | 3/2018 | Randhawa et al. |
| 2020/0113573 | A1 | 4/2020 | Shi |
| 2022/0167990 | A1 | 6/2022 | Kuhn |
| 2023/0404584 | A1 | 12/2023 | Yang et al. |
| 2024/0008877 | A1 | 1/2024 | Yang et al. |

FOREIGN PATENT DOCUMENTS

| | | | |
|---|---|---|---|
| CN | 110393564 | A | 11/2019 |
| CN | 110464410 | A | 11/2019 |
| CN | 111281468 | A | 6/2020 |
| CN | 213430373 | U | 6/2021 |
| CN | 113288379 | A | 8/2021 |
| CN | 114431917 | A | 5/2022 |
| CN | 114431918 | A | 5/2022 |
| CN | 217338676 | U | 9/2022 |
| CN | 115137438 | A | 10/2022 |
| CN | 115670592 | A | 2/2023 |
| CN | 116115288 | A | 5/2023 |
| CN | 116269603 | A | 6/2023 |
| CN | 219422895 | U | 7/2023 |

OTHER PUBLICATIONS

Written Opinion in PCT/CN2024/080849 mailed on Jun. 12, 2024, 6 pages.

HEMOSTATIC CLIP ASSEMBLY AND TWO-PIECE FORCEPS

CROSS-REFERENCE TO RELATED APPLICATIONS

This application is a Continuation-in-part of International Application No. PCT/CN2024/080849, filed on Mar. 8, 2024, which claims priority to Chinese Applications No. 202320441753.0 and No. 202310225453.3, filed on Mar. 10, 2023, the entire contents of each of which are incorporated herein by reference.

TECHNICAL FIELD

The present disclosure relates to the technical field of medical instruments, and in particular to a hemostatic clip assembly and two-piece forceps.

BACKGROUND

The hemostatic clip usually compresses the bleeding site using the mechanical pressure generated by the closure of two clip pieces to block bleeding; then the two clip pieces are separated by an external control handle, such that the clip pieces are left in the body to achieve continuous hemostasis.

According to the hemostatic clip in the prior art, the two clip pieces are of an integrated structure, and the rear ends of the clip pieces are solidly attached. During the frequent opening and closing of the clip pieces, the connection between the rear ends of the clip pieces is subjected to a relatively great force, which causes a risk of fracture. In addition, proximal ends of the clip pieces having the integrated structure do not move freely, no new connection structure can be processed on the clip pieces, and an applicator handle may only be connected to the proximal end of each clip piece through a C-shaped fitting portion. When the applicator handle is separated from each clip piece, an opening of the C-shape fitting portion increases, and it is difficult to restore the C-shape fitting portion to a standard C-shape structure to be stably connected with the rear end of each clip piece again, which leads to the poor recoverability of the applicator handle. Furthermore, a deformable structure needs to be additionally arranged to lock the clip pieces with a casing in a closed state, which increases the production cost.

In addition, in the traditional structure, the applicator handle is connected to the proximal end of each clip piece, the locking of the clip pieces and the casing and the separation of the applicator handle from the clip piece need to overcome respective resistance. That is, it needs to overcome double resistance to complete releasing of the clip pieces, which makes it difficult to control the timing of the locking of the clip pieces and the casing. Accordingly, the sequence of the locking of the clip pieces and the casing and the separation of the clip pieces and the applicator handle is ensured requiring accurate structural design and material selection, otherwise, the phenomenon that the clip pieces and the casing are not locked after the applicator handle is separated may occur. Therefore, the processing precision requirements are high.

In view of the foregoing, it is desirable to provide a hemostatic clip assembly and two-piece forceps that are easy to disassemble, fabricate and process, which allows for flexible control and locking of the clip pieces.

SUMMARY

One or more embodiments of the present disclosure provide a hemostatic clip assembly. The hemostatic clip assembly may comprise a sleeve, two-piece forceps, and a pulling device connected with the two-piece forceps. The two-piece forceps and the pulling device may be at least partially located within the sleeve. The two-piece forceps may include a fixing member and two clip pieces connected through the fixing member and arranged opposite to each other. Each of the two clip pieces may include a first clip section close to a distal end and a second clip section close to a proximal end. The fixing member may be provided through the second clip section. The second clip section may be provided with a first locking mechanism and a second locking mechanism, two second locking mechanisms being arranged opposite to each other. An end of the pulling device may be detachably connected with the two-piece forceps through the second locking mechanisms and make the two first locking mechanisms close to each other. The sleeve may be provided with a third locking mechanism. The two-piece forceps may move toward the proximal end under an action of the pulling device when the pulling device is disconnected from the second locking mechanisms. The sleeve may make the two first clip sections of the two clip pieces close to each other. The two first locking mechanisms may move away from each other after the pulling device is disconnected from the second locking mechanisms. The first locking mechanism may cooperate with the third locking mechanism in securing the two-piece forceps to the sleeve. The pulling device may include a rod portion and a connection portion connected with each other. The connection portion may cooperate with the second locking mechanisms to connect the pulling device to the two-piece forceps. The connection portion is capable of deforming and disconnecting from the second locking mechanisms under a tensile force toward the proximal end.

One or more embodiments of the present disclosure provide two-piece forceps. The two-piece forceps may comprise a fixing member and two clip pieces connected through the fixing member and arranged opposite to each other. Each of the two clip pieces may include a clip arm section and a clip tail section which extend from a distal end to a proximal end. The clip arm section may include a first clip section close to the distal end and a second clip section close to the proximal end. The fixing member may connect ends of the two clip tail sections close to the second clip sections. One end of the clip tail section away from the second clip section may be provided with a first locking mechanism. The clip tail section may further include a second locking mechanism provided between the fixing member and the first locking mechanism. One end of a pulling device of a hemostatic clip may be detachably connected with the two-piece forceps through the second locking mechanism. In a natural state, ends of the two clip tail sections of the two clip pieces away from the second clip sections may be disconnected. An opening may be formed at the distal ends of the two first clip sections of the two clip pieces.

BRIEF DESCRIPTION OF THE DRAWINGS

The present disclosure will be further illustrated by way of exemplary embodiments, which will be described in detail by means of the accompanying drawings. These embodiments are not limiting, and in these embodiments, the same numbering indicates the same structure, wherein.

DETAILED DESCRIPTION

Figure 1:
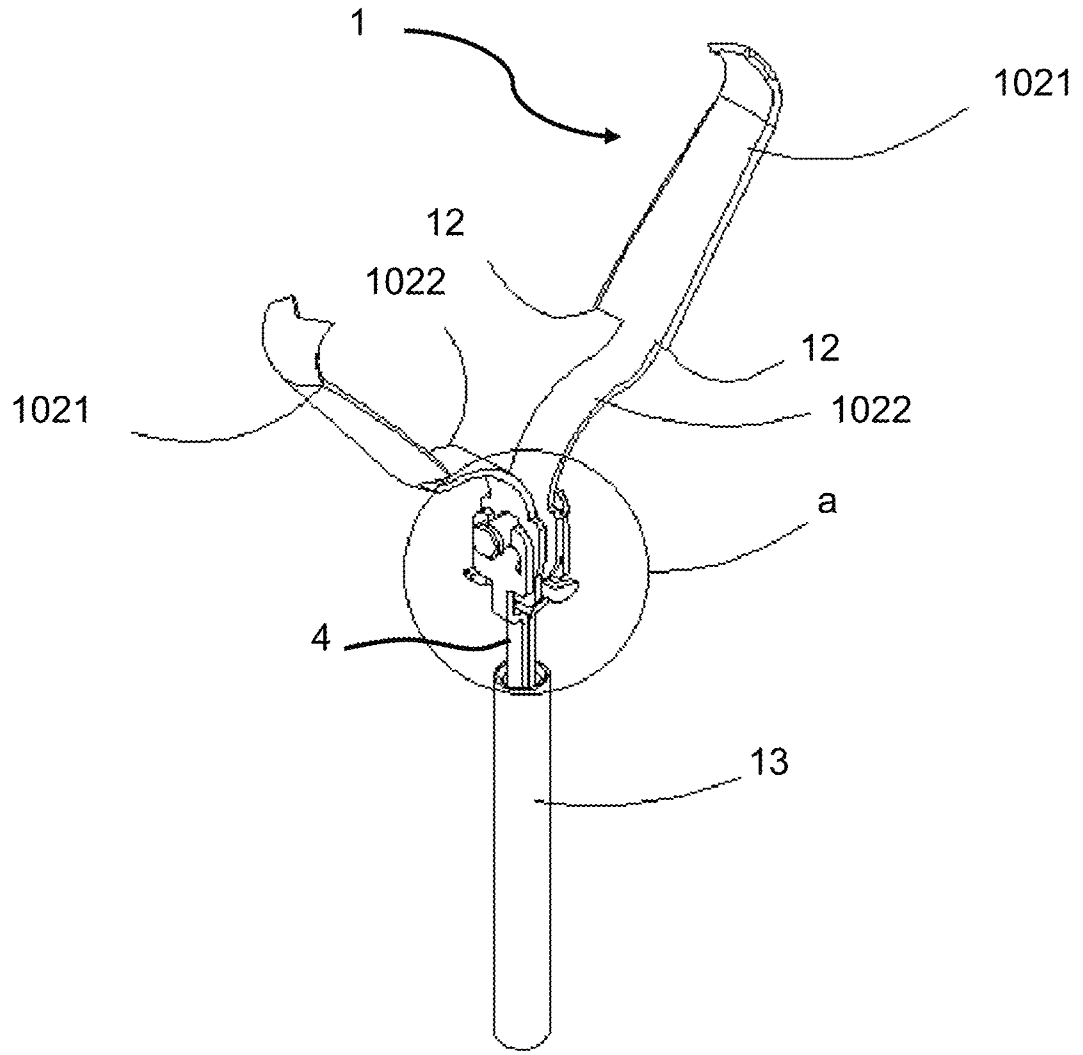
FIG. 1 is a schematic diagram illustrating an assembly of two-piece forceps and a pulling device according to some embodiments of the present disclosure.

In order to more clearly illustrate the technical solutions of the embodiments of the present disclosure, the accompanying drawings required to be used in the description of the embodiments are briefly described below. Obviously, the accompanying drawings in the following description are only some examples or embodiments of the present disclosure, and it is possible for a person of ordinary skill in the art to apply the present disclosure to other similar scenarios in accordance with these drawings without creative labor. Unless obviously obtained from the context or the context illustrates otherwise, the same numeral in the drawings refers to the same structure or operation.

It should be understood that the terms “system,” “device,” “unit” and/or “module” used herein are a way to distinguish between different components, elements, parts, sections, or assemblies at different levels. However, the terms may be replaced by other expressions if other words accomplish the same purpose.

As shown in the present disclosure and in the claims, unless the context clearly suggests an exception, the words “one,” “a,” “an,” “one kind”, and/or “the” do not refer specifically to the singular, but may also include the plural. Generally, the terms “including” and “comprising” suggest only the inclusion of clearly identified steps and elements, however, the steps and elements that do not constitute an exclusive list, and the method or apparatus may also include other steps or elements.

Figure 2:
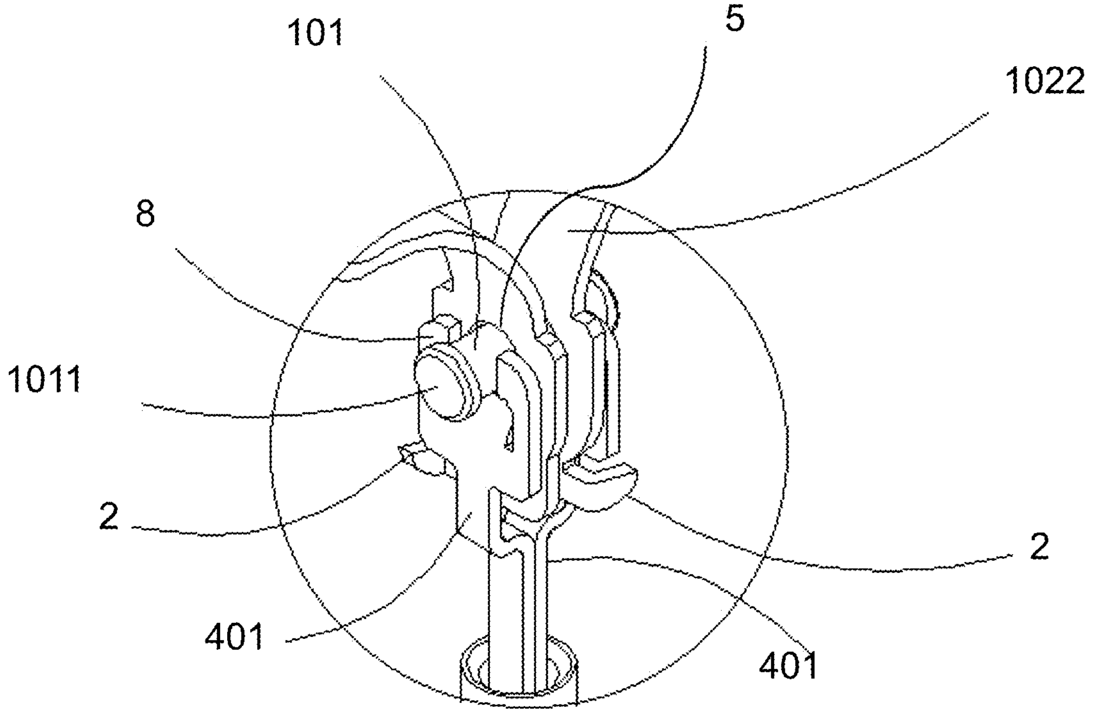
FIG. 2 is a schematic diagram illustrating an enlargement at a in FIG. 1 according to some embodiments of the present disclosure.
Figure 3:
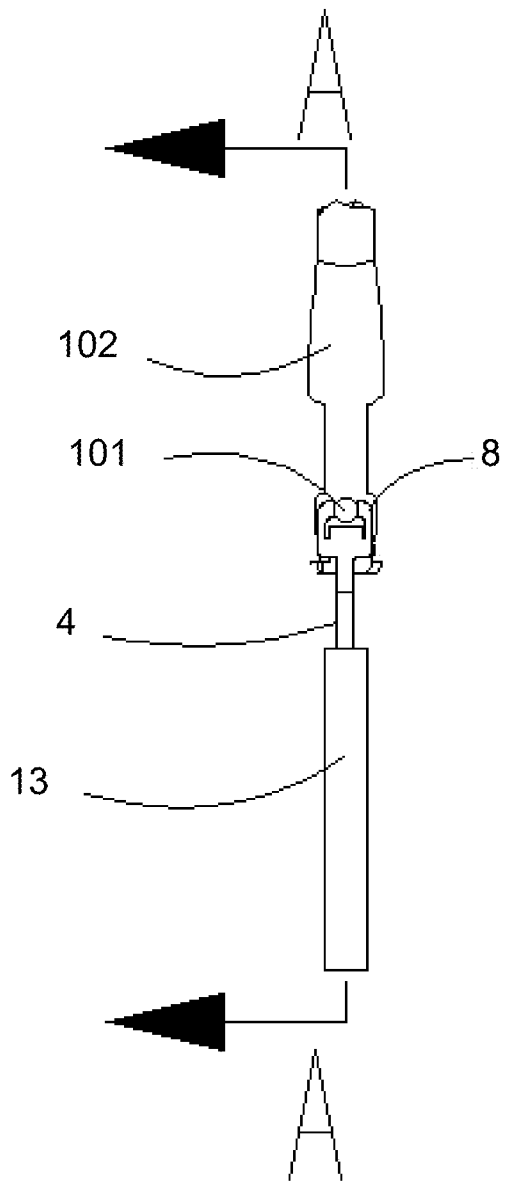
FIG. 3 is schematic diagram illustrating a side view of FIG. 1 according to some embodiments of the present disclosure.
Figure 4:
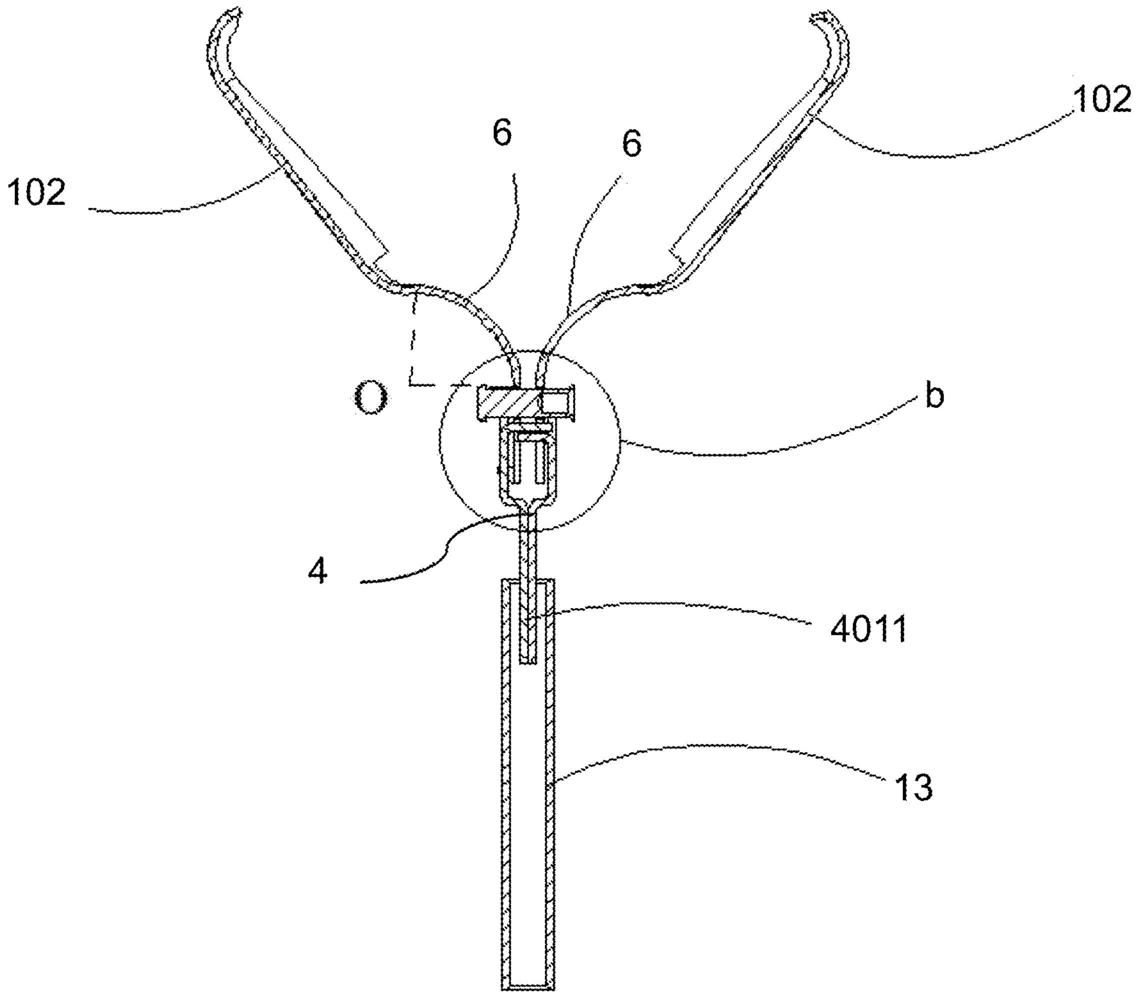
FIG. 4 is a schematic diagram illustrating an A-A direction sectional view of FIG. 3 according to some embodiments of the present disclosure.
Figure 5:
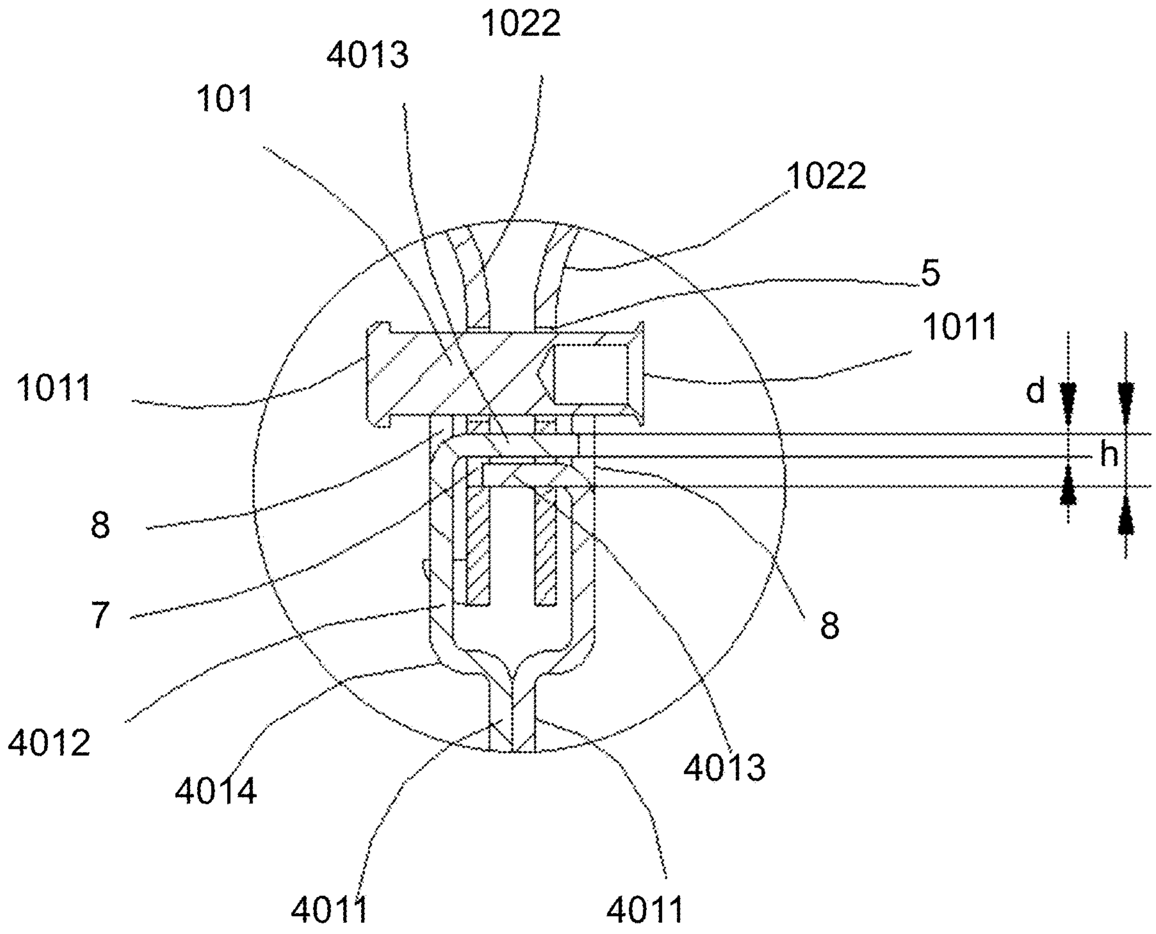
FIG. 5 is a schematic diagram illustrating an enlargement at b in FIG. 4 according to some embodiments of the present disclosure.
Figure 6:
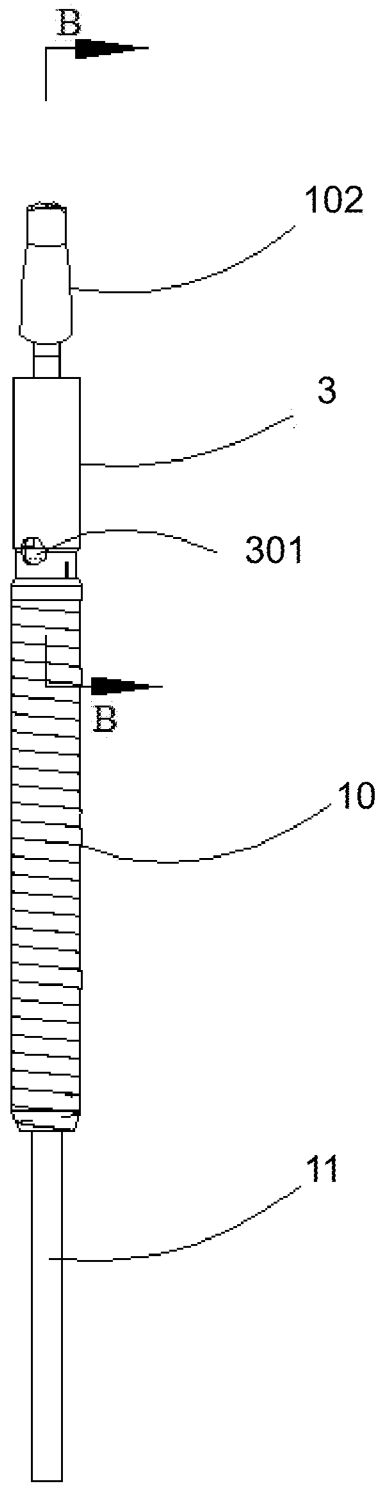
FIG. 6 is a schematic diagram illustrating a main view of a hemostatic clip in a closed state according to some embodiments of the present disclosure.

FIG. 1 is a schematic diagram illustrating an assembly of two-piece forceps and a pulling device according to some embodiments of the present disclosure. FIG. 2 is a schematic diagram illustrating an enlargement at a in FIG. 1 according to some embodiments of the present disclosure. FIG. 3 is schematic diagram illustrating a side view of FIG. 1 according to some embodiments of the present disclosure. FIG. 4 is a schematic diagram illustrating an A-A direction sectional view of FIG. 3 according to some embodiments of the present disclosure. FIG. 5 is a schematic diagram illustrating an enlargement at b in FIG. 4 according to some embodiments of the present disclosure. FIG. 6 is a schematic diagram illustrating a main view of a hemostatic clip in a closed state according to some embodiments of the present disclosure.

The “proximal end” and “distal end” referred to in the embodiments of the present disclosure may denote a direction. For example, in an axial direction of an instrument, the side facing an operator is denoted as the proximal end, and the side for reaching a human body for treatment is denoted as the distal end. The proximal end and the distal end may also denote portions of the structure disposed in corresponding directions, and should not be construed to denote only end portions. For example, the proximal end is an end portion of a clip piece 102 that faces the operator, and the distal end is an end portion of the clip piece 102 that reaches the human body for treatment.

In some embodiments, as shown in FIGS. 1-6, a hemostatic clip assembly may include a sleeve 3, two-piece forceps 1, and a pulling device 4 connected with the two-piece forceps 1. The two-piece forceps 1 and the pulling device 4 may be at least partially located within the sleeve 3. The two-piece forceps 1 may include a fixing member 101 and two clip pieces 102 connected through the fixing member 101 and arranged opposite to each other. Each of the two clip pieces 102 may include a first clip section 1021 close to a distal end and a second clip section 1022 close to a proximal end. The fixing member 101 may be provided through the second clip section 1022. The second clip section 1022 may be provided with a first locking mechanism 2 and a second locking mechanism 7, two second locking mechanisms 2 being arranged opposite to each other. An end of the pulling device 4 may be detachably connected with the two-piece forceps 1 through the second locking mechanisms 7 and make the two first locking mechanisms 2 close to each other. The sleeve 3 may be provided with a third locking mechanism 301. The two-piece forceps 1 may move toward the proximal end under an action of the pulling device 4 when the pulling device 4 is disconnected from the second locking mechanisms 7. The sleeve 3 may make the two first clip sections 1021 of the two clip pieces 102 close to each other. The two first locking mechanisms 2 may move away from each other after the pulling device 4 is disconnected from the second locking mechanisms 7, and the first locking mechanisms 2 may cooperate with the third locking mechanism 301 in securing the two-piece forceps 1 to the sleeve 3.

The hemostatic clip assembly may be configured to clip a target position to stop bleeding. The target position may be a target lesion or bleeding tissue, etc.

The two-piece forceps 1 may be configured to reach the target position of a subject and stop bleeding by clamping.

The sleeve 3 may be configured to accommodate the two-piece forceps 1 and the pulling device 4.

The distal end of the two-piece forceps 1 may be provided with forceps and arranged close to the target position during treatment. In some embodiments, the two-piece forceps 1 may open and close the forceps through displacement of the sleeve 3 and a constraint of an inner diameter within the sleeve 3.

The first clip section 1021 may be close to the target lesion or bleeding tissue and configured to clamp a human tissue for compression hemostasis. In some embodiments, ends of the two first clip sections 1021 may be close to each other, as shown in FIG. 1. Ends of the first clip sections 1021 near the distal end may be curved and bent inwardly to form the structure of forceps.

The second clip sections 1022 may be connected with the pulling device 4. In some embodiments, the second clip sections 1022 may extend or retract within the sleeve 3. The second clip sections 1022 may be curved in whole or in part. The two clip pieces 102 may be arranged side by side, and backs of curved portions of the second clip sections 1022 may be arranged opposite to each other. For example, as shown in FIG. 4, when the second clip sections 1022 are curved in part, curved sections 6 may be provided at ends close to the first clip sections 1021. The distal end of the second clip sections 1022 may be approximately C-shaped.

In some implementations, the two-piece forceps 1 may include a free state and a closed state. The free state is a state in which the first clip sections 1021 of the two-piece forceps 1 are free to move closer to or farther away. The closed state is a state in which the first clip sections 1021 of the two-piece forceps 1 remain close to each other. In the free state, the first clip sections 1021 of the two clip pieces 102 may be in an open state, and the second clip sections 1022 may be partially retracted within the sleeve 3. When constrained by the inner diameter of the sleeve 3, the first clip sections 1021 of the two clip pieces 102 may be closed. For example, when pulling back the two-piece forceps 1 into the sleeve 3 until the second clip sections 1022 are fully retracted within the sleeve 3, the two first clip sections 1021 are driven to gradually close. As another example, when gradually pushing the two-piece forceps 1 out of the sleeve 3, the distal ends of the two second clip sections 1022 are gradually released from the constraint of the sleeve 3, and the two first clip sections 1021 gradually open.

Figure 9:
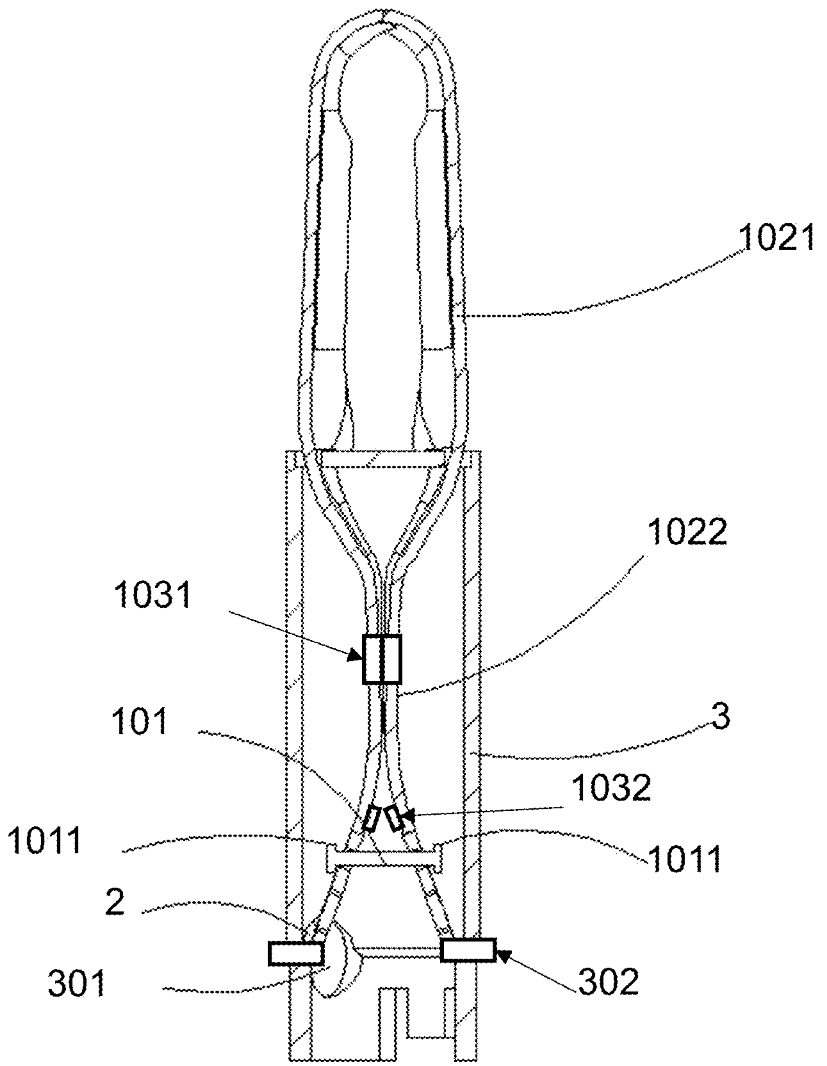
FIG. 9 is a schematic diagram illustrating a state of a hemostatic clip that remains in a human body after being released according to some embodiments of the present disclosure.

The first locking mechanisms 2 may be configured to lock the ends of the second clip sections 1022. The first locking mechanisms 2 may be constrained to be close to each other by the pulling device 4 in the closed state and move away from each other in the free state. The first locking mechanisms 2 may be located at the proximal ends of the clip pieces 102. When the second clip sections 1022 are open, the first locking mechanisms 2 have the largest lateral movement distance, thereby ensuring that the first locking mechanisms 2 cooperate with the sleeve 3 (as shown in FIG. 9). In some embodiments, the first locking mechanisms 2 may be disposed on the second clip sections 1022.

In some embodiments, the first clip sections 1021 of the two clip pieces 102 may be separated in the free state in various ways to make the two first clip sections 1021 form an opening. For example, the two first clip sections 1021 forming the opening may be achieved by an elastic force of the second clip sections 1022, or by an additional reset structure. For example, a reset spring may be connected between the proximal ends of the two second clip sections 1022, and in the free state, the reset spring makes the proximal ends of the two second clip sections 1022 close to each other such that the distal ends of the two first clip sections 1021 are away from each other to form the opening.

In some embodiments, a center of curvature of one of the second clip sections 1022 and a center of curvature of the other of the second clip sections 1022 may be located on two sides of positions at which relative connection points of the backs of the curved portions of the two second clip sections are located, respectively; in the free state, when the backs of the curved portions of the two second clip sections 1022 fit, due to the design of the curved feature and the lever principle, the connection points of the backs of the curved portions of the two second clip sections 1022 gradually move toward the distal ends or the proximal ends, and the proximal ends of the two second clip sections 1022 may outwardly open or inwardly close. As the proximal ends of the second clip sections 1022 open outwardly, the two first clip sections 1021 gradually move close to each other such that the two-piece forceps 1 are in the closed state. For example, as shown in FIG. 1 and FIG. 4, the curved sections 6 of the clip pieces 102 are located on the second clip sections 1022. Taking the clip piece 102 on the left side of FIG. 4, as an example, a center of curvature of the curved section 6 on the left side is a point O. The point O and the second clip section 1022 on the right side are located on two sides of the second clip section 1022 on the left side, respectively, i.e., the curved sections 6 of the two second clip sections 1022 are curved outwardly (i.e., curved in opposite directions).

In some embodiments, as shown in FIG. 1, a width of each of the first clip sections 1021 may be greater than a width of each of the second clip sections 1022, such that a lateral boss 12 may be formed at the proximal end of each of the first clip sections 1021. When the two-piece forceps 1 are in the closed state, the second clip sections 1022 may be at least partially located in the sleeve 3, the first clip sections 1021 may be located outside the sleeve 3, and the lateral bosses 12 may abut against the distal ends of the sleeve 3 to inhibit the two-piece forceps 1 from continuing to move in a proximal direction.

In some embodiments, the second clip sections 1022 may be curved, while the first clip sections 1021 may have straight longitudinal axes. When the two-piece forceps 1 are in the closed state, a maximum spacing of a clamping space formed between the two first clip sections 1021 may not be less than an outer diameter of the sleeve 3, such that the backs of the curved portions of the second clip sections 1022 and the distal ends of the sleeve 3 may abut against each other, preventing the two-piece forceps 1 from being further dragged by the pulling device 4 and preventing the two-piece forceps 1 from being separated from the sleeve 3.

The fixing member 101 may be configured to connect the two clip pieces 102 to synchronize the movement of the two clip pieces 102.

In some embodiments, constrained by the inner diameter of the sleeve 3, the second clip sections 1022 of the two clip pieces 102 always have portions close to each other within the sleeve 3. When the two first clip sections 1021 are located outside the sleeve 3, the curved sections 6 of the two second clip sections 1022 are located outside the sleeve 3, rear portions of the second clip sections 1022 are constrained within the sleeve 3, and the curved sections 6 of the second clip sections 1022 open outside the sleeve 3, such that the first clip sections 1021 open, and the two-piece forceps 1 are in the free state. When the two second clip sections 1022 are dragged toward the proximal ends by the pulling device 4 inside the sleeve 3, the curved sections 6 of the two second clip sections 1022 fit and extrude inside the sleeve 3, the connection points of the backs of the curved portions of the two second clip sections 1022 gradually move toward the first clip sections 1021, and the proximal ends of the second clip sections 1022 gradually tend to open according to the lever principle. When the pulling device 4 is disconnected from the second locking mechanisms 7, the pulling device 4 also releases restraining the proximal ends of the second clip sections 1022, and the proximal ends of the two second clip sections 1022 are eventually away from each other such that the first locking mechanisms 2 cooperate with the third locking mechanism 301. In this case, the two first clip sections 1021 are closed relative to each other, thereby making the two-piece forceps 1 in the closed state.

The two-piece forceps 1 may consist of two independent clip pieces 102, and the production process is simple. The structures of the two independent clip pieces 102 may be the same, which is convenient for batch production. The force at a connection of the two clip pieces 102 is reduced, and no fracture occurs. In addition, the clip pieces 102 may be provided with the first locking mechanism 2, which can realize the locking of the two-piece forceps 1 and the sleeve 3 by deformation of the clip pieces 102, thereby simplifying the structure, and improving the movement synchronization.

In some embodiments, as shown in FIG. 2, the fixing member 101 may be a pin shaft, and each of the second clip sections 1022 may be provided with a shaft hole 5 for the pin shaft to pass through.

In some embodiments, the shaft hole 5 may be provided in a thickness direction of each of the second clip sections 1022. A size of the shaft hole 5 may match a size of the pin shaft.

In some embodiments, the fixing member 101 may be in clearance fitting with the shaft hole 5, i.e., a hole diameter of the shaft hole 5 may be greater than a diameter of the fixing member 101, allowing the second clip sections 1022 to open and close.

In some embodiments, at least one axial end of the pin shaft may be provided with a masking cap 1011, as shown in FIG. 2. The masking cap 1011 may be configured to avoid the pin shaft from detaching from the shaft hole 5. A diameter of the masking cap 1011 may be greater than the diameter of the shaft hole 5. In some embodiments, an axial end of the pin shaft may be provided with the masking cap 1011, and another axial end of the pin shaft may be reamed to avoid disengagement of the pin shaft.

In some embodiments, the two clip pieces 102 can be prevented from running laterally within the sleeve 3 by providing the cooperation of the pin shaft and the shaft hole, such that the two clip pieces 102 move more stably in the axial direction, and the force exerted by the operator on the forceps is relatively stable.

In some embodiments, as shown in FIG. 2 and FIG. 6, the third locking mechanism 301 may be a slot, and the first locking mechanisms 2 may be hooks.

In some embodiments, as shown in FIG. 9, the hooks fit the slot to secure the two-piece forceps 1 in the sleeve 3 when the two second clip sections 1022 are open relative to each other and the first clip sections 1021 are closed relative to each other. The hooks on the two clip pieces 102 may be arranged opposite each other or diagonally.

In some embodiments, a length of the fixing member 101 may be set in a way that the hooks reach the slot of the sleeve 3 when the two second clip sections 1022 are open.

In some embodiments, the third locking mechanism 301 and the second locking mechanisms 7 are not limited to being the slot and the hooks, respectively. For example, the third locking mechanism 301 and the second locking mechanisms 7 may also be a buckle structure such as a ring buckle, an insert buckle, or the like.

The second locking mechanisms 7 refer to devices cooperatively connected with the pulling device 4. In some embodiments, the second locking mechanisms 7 may be cooperatively connected with the pulling device 4 to allow the pulling device 4 to pull the clip pieces 102 toward the proximal ends or push the clip pieces 102 toward the distal ends. In some embodiments, the second locking mechanisms 7 may be provided on the second clip sections 1022.

In some embodiments, the second locking mechanism 7 may be provided between the first locking mechanism 2 and the fixing member 101. The two first locking mechanisms 2 are forced to be close to each other when the pulling device 4 is connected with the second locking mechanisms 7. The two first locking mechanisms 2 are automatically separated when the pulling device 4 is disconnected from the second locking mechanisms 7. The setting of the second locking mechanisms 7 may provide the first locking mechanisms 2 with a relatively large instantaneous release force, which is conducive to quickly cooperating with the third locking mechanism 301 of the sleeve 3; and ensure the accuracy of successive movements, thereby avoiding early release of the first locking mechanisms 2.

The pulling device 4 refers to a device for pulling the clip pieces 102 to move. In some embodiments, the pulling device 4 may be removably connected with the second locking mechanisms 7, as shown in FIG. 4 and FIG. 5. In some embodiments, when the pulling device 4 pulls the second clip sections 1022 to move toward the proximal ends, the pulling device 4 may be disconnected from the second locking mechanisms 7 when a preset condition is reached. The preset condition may be that a tensile force reaches a preset force.

Figure 7:
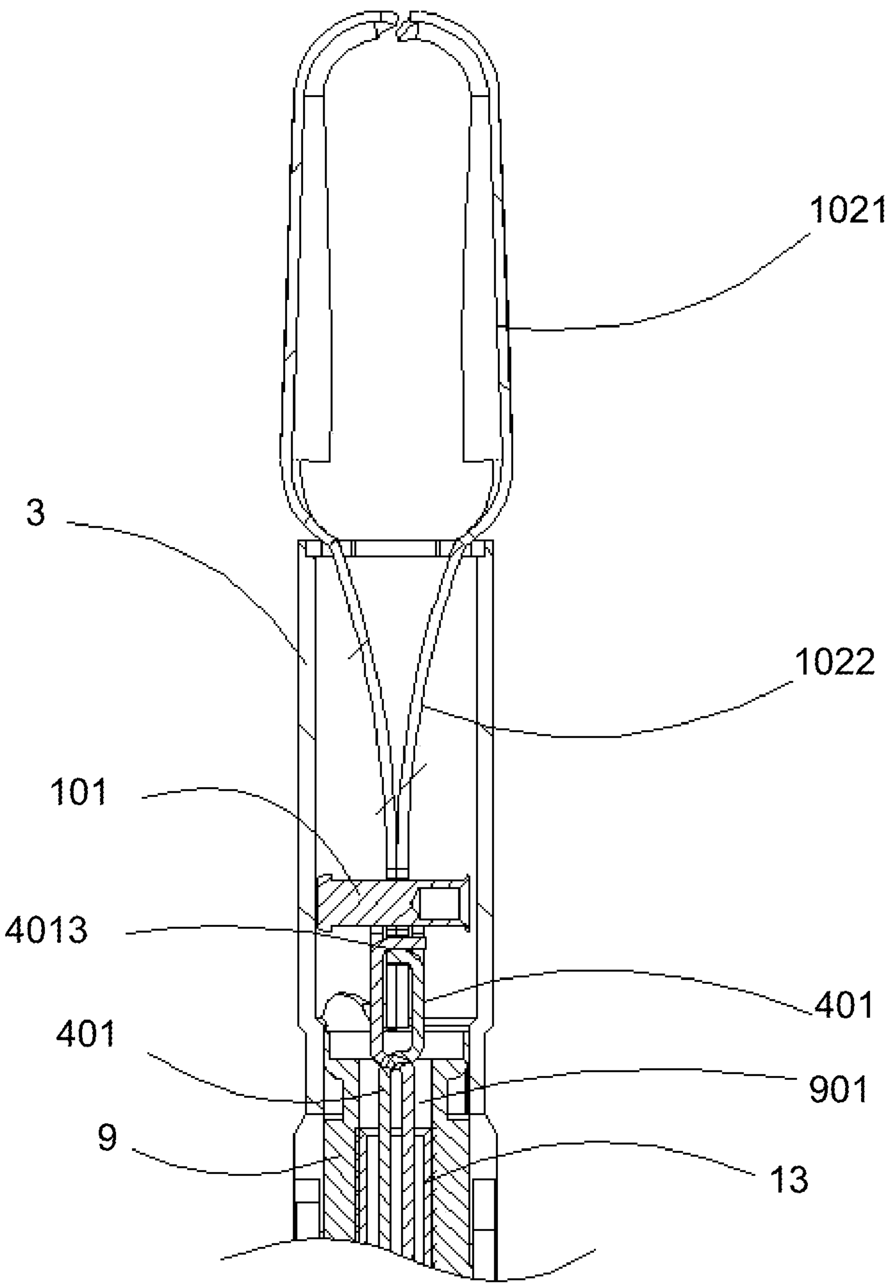
FIG. 7 is a schematic diagram illustrating a B-B direction sectional view of FIG. 6 according to some embodiments of the present disclosure.

FIG. 7 is a schematic diagram illustrating a B-B direction sectional view of FIG. 6 according to some embodiments of the present disclosure.

Figure 8:
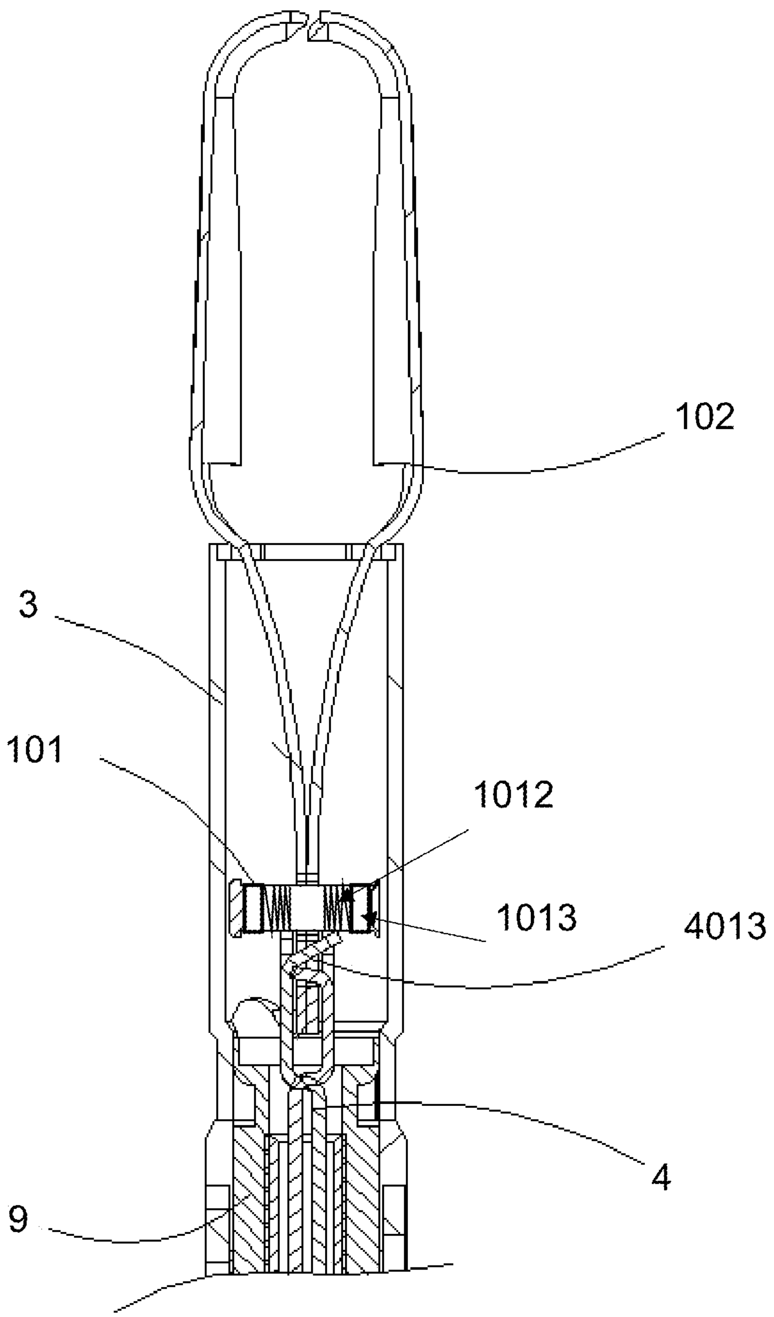
FIG. 8 is a schematic diagram illustrating a B-B direction sectional view of a hemostatic clip in a view of FIG. 6 when a pulling device deforms according to some embodiments of the present disclosure.

FIG. 8 is a schematic diagram illustrating a B-B direction sectional view of a hemostatic clip in a view of FIG. 6 when a pulling device deforms according to some embodiments of the present disclosure.

FIG. 9 is a schematic diagram illustrating a state of a hemostatic clip that remains in a human body after being released according to some embodiments of the present disclosure.

In some embodiments, when the pulling device 4 cooperates with the second locking mechanisms 7, the pulling device 4 clamps and pulls the two second clip sections 1022 close to each other. As the pulling device 4 pushes the two-piece forceps 1 toward the distal end of the sleeve 3, the second clip sections 1022 are gradually pushed out of the sleeve 3 and the two first clip sections 1021 open freely (as shown in FIG. 1). When the two-piece forceps 1 are pulled toward the proximal end of the sleeve 3 to make the second clip sections 1022 gradually enter the sleeve 3, the two first clip sections 1021 are close to each other under the constraint of the diameter dimension of the sleeve 3, and the two-piece forceps 1 are in a closed clamping state (as shown in FIG. 7). When the pulling device 4 is disconnected from the second third locking mechanisms, the proximal ends of the second clip sections 1022 lose a compression force, the proximal ends of the two second clip sections 1022 are open freely, and the first locking mechanisms 2 obediently clamp on the third locking mechanism 301 (as shown in FIG. 9).

In some embodiments, as shown in FIG. 4 and FIG. 5, the pulling device 4 may include a rod portion 4011 and a connection portion connected with each other. The connection portion may cooperate with the second locking mechanisms 7.

The rod portion 4011 may be located at the proximal end of the pulling device 4 and at least partially located within the sleeve 3.

The connection portion may be located at the distal end of the pulling device 4. The connection portion may cooperate with the second locking mechanisms 7 to connect the pulling device 4 to the two-piece forceps 1. The connection portion is capable of deforming and disconnecting from the second locking mechanisms 7 under a tensile force toward the proximal end. In some embodiments, the connection portion may be a closed claw structure in the free state, and the closed claw structure may deform and open under the tensile force to be disconnected from the second locking mechanisms 7.

In some embodiments, each of the second locking mechanisms 7 may be a matching hole, and the connection portion may include an insert plate 4013 that cooperates with the matching hole.

In some embodiments, as shown in FIGS. 3-5, the matching hole may be disposed in a thickness direction of the second clip section 1022, and the matching holes of the two second clip sections 1022 may be arranged opposite each other. In some embodiments, the matching hole may be in various shapes. For example, the matching hole may be a waist-shaped hole, a square hole, a triangular hole, or the like. The matching hole may be provided between the pin shaft and the hook.

In some embodiments, the rod portion 4011 may be disposed at the proximal end of the pulling device 4, and the insert plate 4013 may be connected with the rod portion 4011. When the insert plate 4013 fits the matching hole, an angle may be formed between a surface of the insert plate 4013 and a surface (i.e., a surface with a relatively large area) of the rod portion 4011. The insert plate 4013 may be formed by laser cutting from the rod portion 4011 and bending to ae side, or the insert plate 4013 and the rod portion 4011 may be independent of each other and secured by welding or riveting, etc., so as to make the insert plate 4013 fit the matching hole.

In some embodiments, as shown in FIG. 5 and FIG. 8, the matching hole may be open in a horizontal direction, and the insert plate 4013 may be proximally perpendicular to the rod portion 4011. When the pulling device 4 is pulled toward the proximal end, as the two-piece forceps 1 are constrained by the sleeve 3, the insert plate 4013 may be gradually pulled to a vertical shape until being pulled out of the matching hole.

In some embodiments, a wall surface of an end of the matching hole away from the first clip section 1021 may be a plane, and an inner wall of the matching hole may for a smooth transition with an outer sidewall of the matching hole, thereby pulling out the insert plate 4013 using less effort.

In some embodiments, two insert plates 4013 may be provided, and the two insert plates 4013 may be inserted through the matching holes in the two second clip sections 1022, respectively. A baffle plate 4012 may be connected between each of the insert plates 4013 and the rod portion 4011, and the baffle plate 4012 may press the two second clip sections 1022 together, such that when the pulling device 4 is pulled toward the proximal end and is subjected to resistance, the baffle plates 4012 on two sides may open to the two sides.

In some embodiments, the two baffle plates 4012 may be connected to the same rod portion 4011, and sizes of the matching holes may match sizes of the insert plates. For example, as shown in FIG. 5, a height of the matching hole is denoted as h and a thickness of the insert plate 4013 is denoted as d. If the height h of the matching hole is too large, a gap may be formed between the insert plate 4013 and an inner side of the matching hole, and the two-piece forceps 1 do not respond to the action of the pulling device 4 in time when pulling or pushing the pulling device 4. When there are two insert plates 4013 fitting the matching holes simultaneously, the height h of each matching hole is slightly greater than a sum of the thicknesses d of the two insert plates 4013 (as shown in FIG. 5), such that the two insert plates 4013 fit the inner sides of the matching holes.

In some embodiments, the two insert plates 4013 may be arranged in the matching holes in at least one of a parallel opposite arrangement, a V-shaped arrangement, a herringbone arrangement, or a figure-of-eight arrangement.

Figure 10:
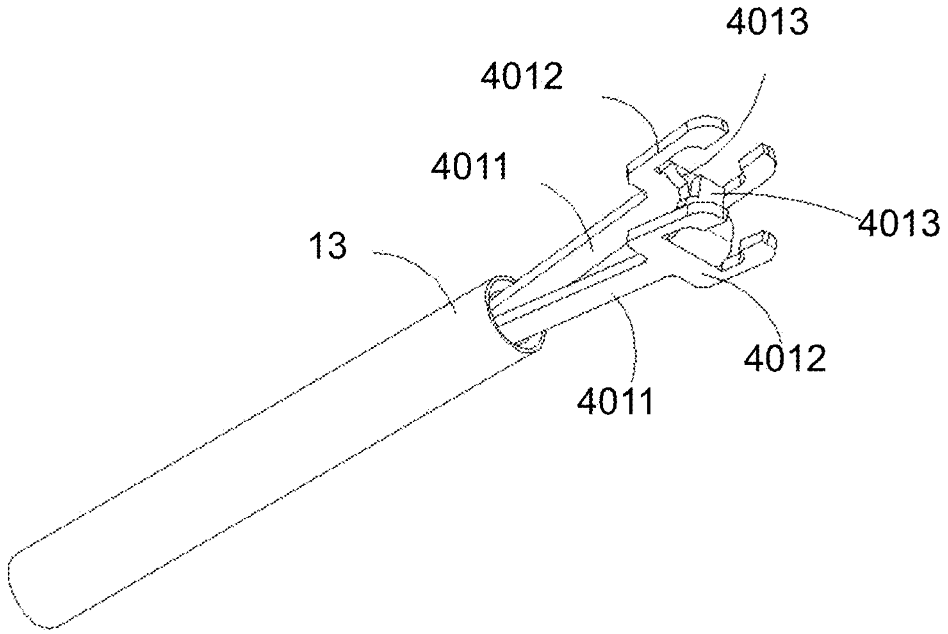
FIG. 10 is a schematic structural diagram illustrating a pulling device according to some embodiments of the present disclosure.
Figure 11:
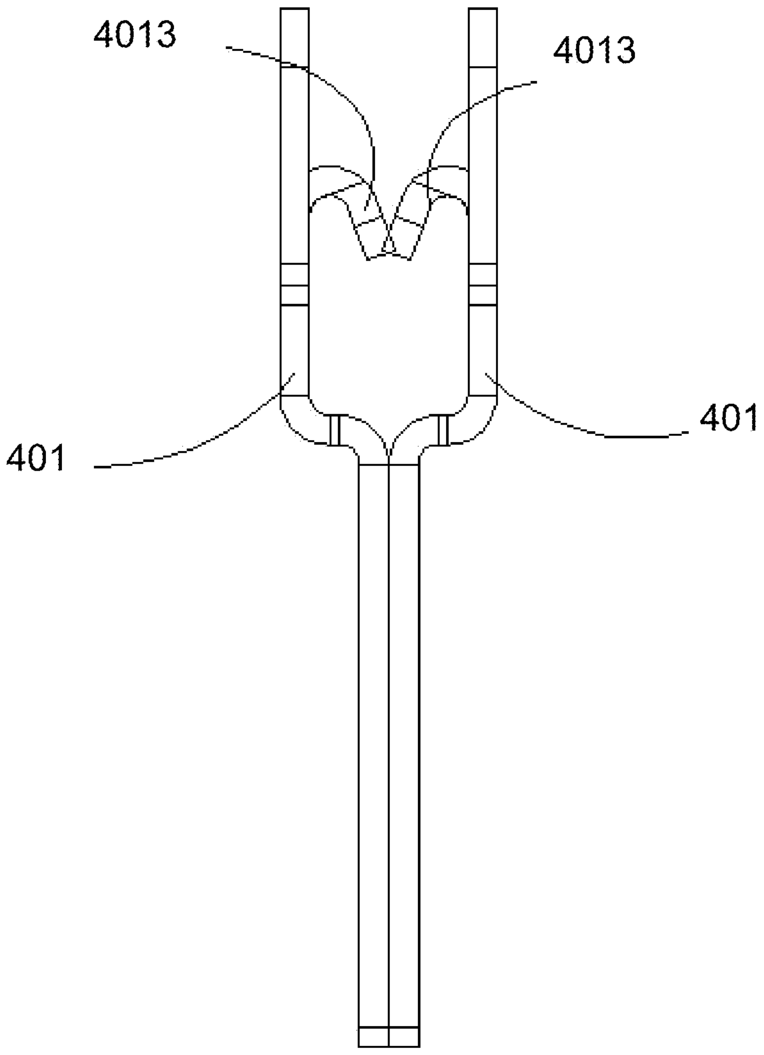
FIG. 11 is a schematic diagram illustrating a pulling device when insert plates are arranged in a V-shaped arrangement according to some embodiments of the present disclosure.
Figure 12:
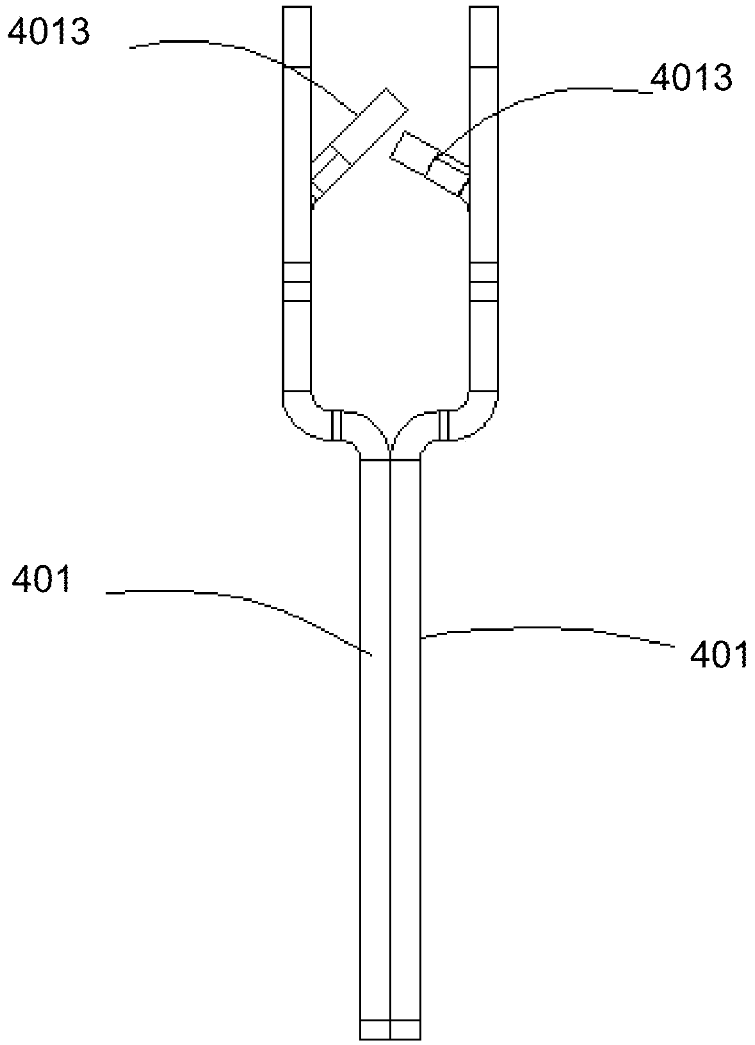
FIG. 12 is a schematic diagram illustrating a pulling device when insert plates are arranged in a herringbone arrangement according to some embodiments of the present disclosure.
Figure 13:
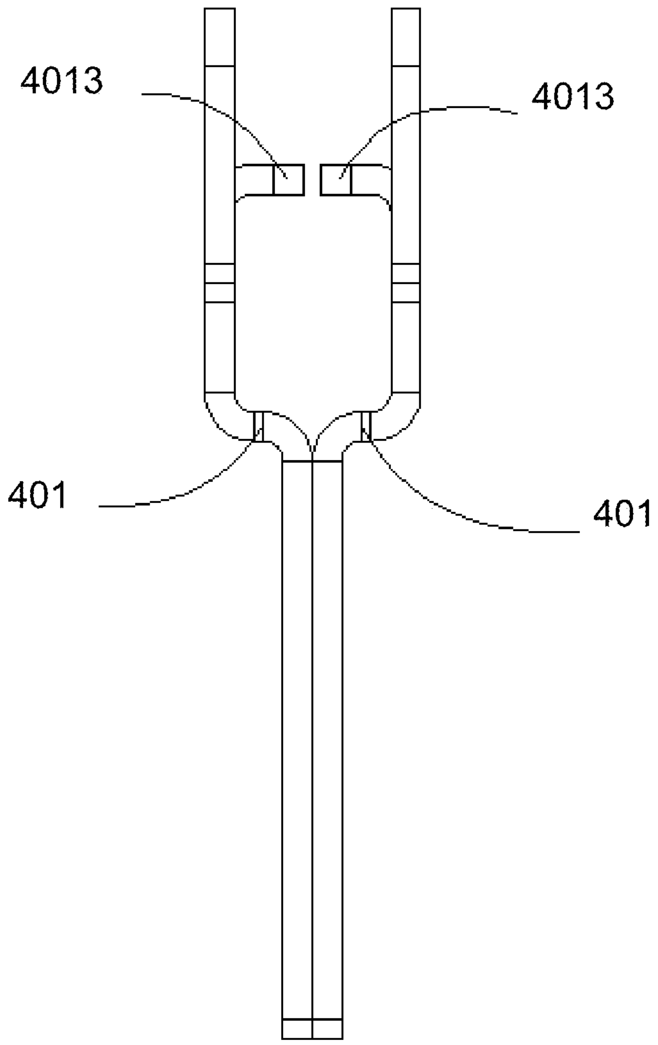
FIG. 13 is a schematic diagram illustrating a pulling device when insert plates are arranged in a horizontal alignment arrangement according to some embodiments of the present disclosure.
Figure 14:
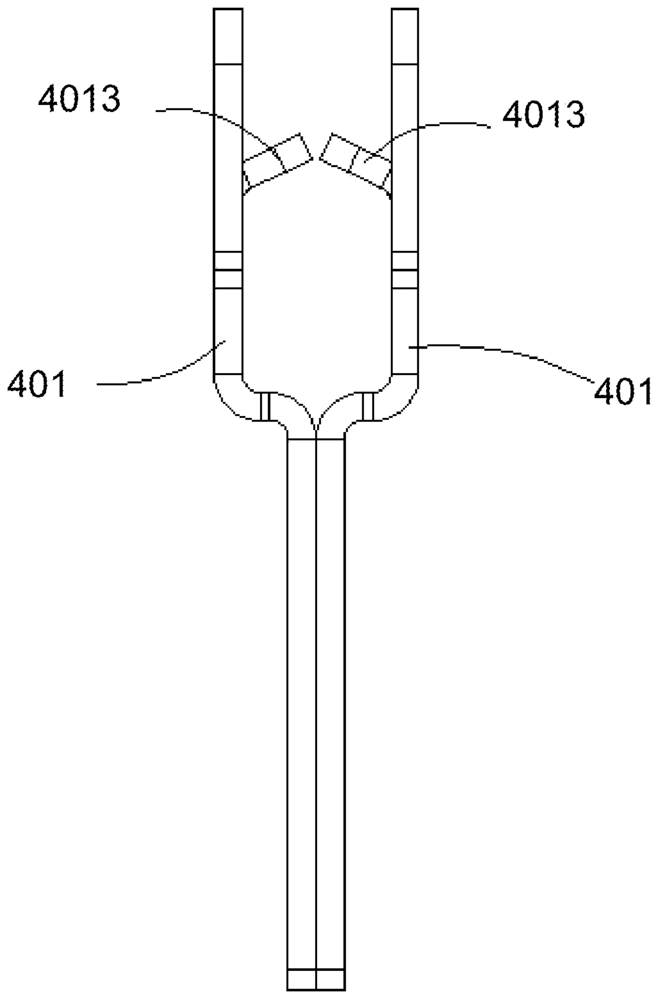
FIG. 14 is a schematic diagram illustrating a pulling device when insert plates are arranged in a figure-of-eight arrangement according to some embodiments of the present disclosure.

FIG. 10 is a schematic structural diagram illustrating a pulling device according to some embodiments of the present disclosure. FIG. 11 is a schematic diagram illustrating a pulling device when insert plates are arranged in a V-shaped arrangement according to some embodiments of the present disclosure. FIG. 12 is a schematic diagram illustrating a pulling device when insert plates are arranged in a herringbone arrangement according to some embodiments of the present disclosure. FIG. 13 is a schematic diagram illustrating a pulling device when insert plates are arranged in a horizontal alignment arrangement according to some embodiments of the present disclosure. FIG. 14 is a schematic diagram illustrating a pulling device when insert plates are arranged in a figure-of-eight arrangement according to some embodiments of the present disclosure.

In some embodiments, a parallel opposite arrangement may include a horizontal alignment (as shown in FIG. 13) arrangement and a stacked arrangement (as shown in FIG. 10). When the pulling device 4 is not pulled, the two insert plates 4013 may abut against the matching holes and do not disconnect from the matching holes. In some embodiments, the two insert plates may be arranged in the V-shaped arrangement, as shown in FIG. 11. In some embodiments, the two insert plates may be arranged in the herringbone arrangement, as shown in FIG. 12. In some embodiments, the two insert plates may be arranged in the figure-of-eight arrangement, as shown in FIG. 14.

The two baffle plates 4012 may be connected to the same rod portion 4011, the baffle plates 4012 and the insert plates 4013 are difficult to open laterally, and the rod portion 4011 and the baffle plates 4012 are difficult to integrate into one piece. If the rod portion 4011 and the baffle plates 4012 are fixedly connected later, the connection between the rod portion 4011 and the baffle plates 4012 is easily disconnected.

In some embodiments, as shown in FIG. 2 and FIG. 5, the pulling device 4 may include two pulling plates 401 provided on two sides of the two second clip sections 1022, respectively, and each of the two pulling plates 401 may include the rod portion 4011 and the connection portion.

In some embodiments, each of the two pulling plates 401 may include the rod portion 4011 located at a proximal end and the connection portion located at a distal end. In some embodiments, the two pulling plates 401 may be disposed between the two second clip sections 1022.

In some embodiments, as shown in FIG. 10, each of the two pulling plates 401 may include the rod portion 4011, the baffle plate 4012, and the insert plate 4013. An arrangement direction of the two pulling plates 401 may be parallel to an axial direction of the fixing member 101. In some embodiments, when the pulling plates 401 are pulled, the baffle plates 4012 and the insert plates 4013 may be bent in a direction of thin walls of the pulling plates 401, and the pulling devices 4 may be disconnected from the two-piece forceps 1. More descriptions regarding the insert plates 4013 and the baffle plates 4012 may be found in the related descriptions above.

In some embodiments, the pulling device 4 may consist of two separate pulling plates 401, and the rod portion 4011, the baffle plate 4012, and the insert plate 4013 disposed on each of the two pulling plates 401 may be integrally molded, such that no fracture occurs during bending and deforming. The distal ends of the two pulling plates 401 may be freely open when the pulling device 4 is ready to disconnect from the second locking mechanisms 7. Inserting the two insert plates 4013 into the matching holes may provide a tensile force to the two-piece forceps 1.

In some embodiments, as shown in FIG. 10, the pulling plates 401 may be straight plates. In this case, a distance between the two baffle plates 4012 and a distance between the two rod portions 4011 may be equal, and since the two baffle plates 4012 cannot fit each other, the two pulling plates 401 may be arranged at an angle. In some embodiments, as shown in FIG. 5 and FIG. 12, the pulling plates 401 may be bent, the rod portions 4011 of the pulling plates 401 and the baffle plates 4012 may be connected through bent plates 4014. The two rod portions 4011 fit each other, and the two rod portions 4011 may be partially connected. In some embodiments, the deformation and opening of the baffle plates 4012 are facilitated by the bent plates 4014.

In some embodiments, as shown in FIG. 1 and FIG. 2, the connection portion may further include a limiting plate 8 extending toward the fixing member 101. The limiting plate 8 may be provided with an opening and the opening may face the fixing member 101. The fixing member 101 may be in clearance fitting with the limiting plate 8.

The limiting plate 8 may be configured to limit the second clip sections 1022 and the fixing member 101.

The cooperation of the limiting plate 8 with the fixing member 101 may make symmetry axes of the pulling device 4 and the two-piece forceps 1 to be in the same straight line, which avoids tilting of the pulling device 4. In some embodiments, the limiting plate 8 may be provided between each of the second clip sections 1022 and the masking cap 1011 (or a flared end of the fixing member 101). In some embodiments, the flared end of the masking cap 1011 or the fixing member 101 is a maximum limit position to which the second clip sections 1022 expand outward in a natural state; the limiting plate 8 is a maximum limit position to which the second clip sections 1022 expand outward when the pulling device 4 is connected with the second locking mechanisms 7. Meanwhile, the limiting plate 8 may prevent the fixing member 101 from transverse movement in a left-and-right direction.

In some embodiments, when the pulling device 4 is pulled to move toward the proximal end, the first locking mechanisms 2 are constrained from continuing to open by providing the limiting plate 8, which can prevent locking of the first locking mechanisms 2 and the third locking mechanism 301 in advance before the pulling device 4 is disconnected from the second locking mechanisms 7.

In some embodiments, as shown in FIG. 7, the hemostatic clip assembly may further include a connection shaft 9 axially limited to the proximal end of the sleeve 3. The connection shaft 9 may be provided with a central shaft 901 for the pulling device 4 to pass through.

The connection shaft may be used for axial limitation of the pulling device 4. The central shaft 901 is a channel structural member located in the middle of the connection shaft 9. In some embodiments, the pulling device 4 is capable of driving the connection shaft 9 to move toward the proximal end of the sleeve 3 to disconnect the connection shaft 9 from the sleeve 3. The connection shaft 9 may hide a connection section of the pulling device 4 to the two-piece forceps 1 within the sleeve 3. In some embodiments, the connection shaft 9 may be tubular. In some embodiments, by fixing the sleeve 13 at the proximal end of the pulling device 4, the sleeve 13 fits the central shaft 901, such that changing the configuration of the connection shaft 9 can be avoided.

In some embodiments, a contact surface between the sleeve 3 and the connection shaft 9 may be a reducing cylindrical surface, such that the connection shaft 9 is extruded at the proximal end of the sleeve 3, and the connection shaft 9 shrinks and deforms and disconnects from the proximal end of the sleeve 3 under the tensile force of the pulling device 4. In some embodiments, the proximal end of the sleeve 3 may also be provided with barbs that butt against an end surface of the connection shaft 9. The barbs may hold the end surface of the connection shaft 9 to prevent the connection shaft 9 from disconnecting. In some embodiments, when the pulling device 4 drives the connection shaft 9 to move toward the proximal end of the sleeve 3, the barbs may be extruded and straightened, and the connection shaft 9 may be disconnected from the proximal end of the sleeve 3.

In some embodiments, each of the two second clip sections 1022 of the clip pieces 102 may be provided with a magnetic sheet.

In some embodiments, at least one set of magnetic sheets may be provided on distal inner walls of the two second clip sections 1022, and magnetic forces of each set of the magnetic sheets may be in opposite directions. Each set of the magnetic sheets may be provided opposite to each other. For example, as shown in FIG. 9, the magnetic sheets 1031 may be provided on upper side inner walls of the two second clip sections 1022, and the magnetic forces of the magnetic sheets 1031 on the two second clip sections 1022 may be in opposite directions.

In some embodiments, at least one set of magnetic sheets may be provided on the proximal inner walls of the two second clip sections 1022, and the magnetic forces of each set of magnetic sheets may be in opposite directions. Each set of magnetic sheets may be provided opposite each other. For example, as shown in FIG. 9, the magnetic sheets 1032 may provided on lower inner sidewalls of the two second clip sections 1022, and the magnetic forces of the magnetic sheets 1032 on the two second clip sections 1022 may be in opposite directions.

The clamping force of the clip pieces can be improved by the magnetic fitting of the magnetic sheets, which makes the clamping more stable.

In some embodiments, the third locking mechanism 301 may be provided with a locking buckle 302. The locking buckle 302 may be configured to be retractably connected with the sleeve 3, as shown in FIG. 9.

In some embodiments, the locking buckle 302 may be remotely controlled by a drawstring 11. When the clip pieces are placed in a target position (e.g., a target lesion or bleeding tissue in a human body) of a subject, the clip pieces may be remotely controlled by the sleeve 3, the drawstring 11, or the like.

For example, as shown in FIG. 9, the third locking mechanism 301 may be a slot, and the slot may be leveled or tilted by remotely controlling rotation of the locking buckle 302 through the drawstring 11. When the slot is tilted, the first locking mechanisms 2 (e.g. hooks) cannot be locked to the slot, the first locking mechanisms 2 are disconnected from the third locking mechanism 301, which in turn makes the sleeve 3 disconnect from the two-piece forceps 1.

In some embodiments, the locking buckle 302 may be partially exposed out of an outer side of the sleeve 3. By toggling the locking buckle 302 located on the outer side of the sleeve 3, the position of the third locking mechanism 301 may be adjusted, thereby adjusting a locking state of the first locking mechanisms 2.

The locking buckle 302 is provided such that the first locking mechanisms 2 at the ends of the second clip sections 1022 are disconnected from the third locking mechanism 301 while reducing the displacement of the clip pieces 102, which avoids improper displacement of the clip pieces 102 that may cause the clip pieces 102 to damage a human tissue near the hemostatic clip.

In some embodiments, when two ends of the fixing member 101 are provided with the masking cap 1011, respectively, telescopic springs 1012 may be symmetrically distributed at inner sides of the masking caps 1011 at the two ends. The telescopic springs 1012 may be configured to passively telescope during a back and forth movement of the clip pieces 102.

When the clip pieces 102 move upward and downward, an opening degree of the clip pieces 102 changes, and the clamping force at a contact position between the fixing member and the clip pieces 102 also changes according to the lever principle, then the elasticity of the telescopic springs changes along with the change in the clamping force.

By measuring the elasticity of the telescopic springs 1012, the clamping force of the clip pieces 102 may be quantified.

In some embodiments, the fixing member 101 may be further provided with at least one force sensor 1013. For example, as shown in FIG. 8, the two ends of the fixing member 101 may be provided with the force sensor 1013, respectively, and the force sensor 1013 may be provided between each of the telescopic springs 1012 and each of the masking caps 1011.

In some embodiments, the at least one force sensor 1013 may be configured to monitor and collect spring force information. The spring force information may include the elasticity of the telescopic springs.

The clamping force of the clip pieces 102 may be quantified based on the collected spring force information, which allows for intuitive monitoring and control of the clamping force during operation.

In some embodiments, the hemostatic clip assembly may further include a processor. The processor may be configured to determine the clamping force of the clip pieces 102 of the hemostatic clip based on the spring force information.

The processor may be a programmable logic controller (PLC) microchip and other microprocessors. The processor may be in communication with the at least one force sensor 1013.

In some embodiments, the processor may obtain the spring force information uploaded by the at least one force sensor 1013 and determine the clamping force of the clip pieces 102 based on a preset force table. The preset force table may include a mapping relationship between the spring force information and the clamping force. The preset force table may be obtained based on experience or experimentation.

In some embodiments, the processor may determine the clamping force based on an application scenario and the spring force information.

The application scenario refers to a surgical scenario in which the hemostatic clip assembly is applied, such as gastrointestinal bleeding, arterial or venous bleeding in a medical/surgical or emergency scenario.

In some embodiments, the processor may obtain the application scenario uploaded by a user based on a user terminal. The processor may be in communication with the user terminal.

The preset force table may be constructed based on different application scenarios. The preset force table may include different application scenarios and the mapping relationship between the spring force information and the clamping force. The processor may determine the clamping force by looking up the preset force table based on the application scenario and the spring force information.

In some embodiments, the fixing member 101 may be provided with an indication member, such as a scale or an indicator light. The user may obtain clamping feedback through the indication member. Taking the indicator light as an example, when the clamping force is greater than a first preset threshold, the indicator light shows a red light; when the clamping force is less than or equal to the first preset threshold and greater than or equal to a second preset threshold, the indicator light shows a green light; when the clamping force is less than the second preset threshold, the indicator light does not light. The second preset threshold may be less than the first preset threshold. The first preset threshold refers to a maximum value of the clamping force, and the second preset threshold refers to a minimum value of the clamping force.

In some embodiments, different application scenarios may correspond to different first preset thresholds and different second preset thresholds, which may be set based on experience or historical data. For example, the maximum value of the spring force information in a historical operation record corresponding to a certain application scenario in which the hemostatic effect is abnormal (e.g., when the hemostatic effect is poor) due to too low a clamping force is counted as the second preset threshold corresponding to the application scenario. The minimum value of the spring force information in case of abnormal hemostasis (e.g., additional damage to a living tissue) due to excessive clamping force is counted as the first preset threshold corresponding to the application scenario. The same is true for other application scenarios.

The clamping force is determined by determining the spring force information, and the feedback is given based on the indication member, such that the user intuitively obtains the real-time force, and makes adjustment accordingly, thereby improving the clamping safety, and avoiding accidents due to improper clamping force. Meanwhile, the telescopic springs are simple in structure without additional cost. The effect of different application scenarios on the clamping force is considered, which further improves the safety of the operation and the applicability of the hemostatic clip assembly.

In some embodiments, the processor may be configured to: determine whether a clamping anomaly exists based on the spring force information.

The clamping anomaly may include the damage to the living tissue caused by unstable clamping (e.g., a force fluctuation), loose clamping, excessive clamping force of the clip pieces 102, etc.

For example, in response to determining that a value of the spring force information is greater than or equal to a preset pressure threshold, the processor may determine the clamping anomaly and provide feedback to the user terminal. The preset pressure threshold may be set based on experience. For example, the preset pressure threshold may be set to the first preset threshold. More descriptions regarding the first preset threshold may be found in the related descriptions above.

As another example, the processor may determine whether the clamping anomaly occurs in the clip pieces 102 based on spring force information collected by different force sensors 1013. For example, the processor may determine that the clamping anomaly occurs in the clip piece 102 in response to determining that a difference between the spring force information on the two sides of the fixing member 101 collected by the force sensors 1013 is greater than a first difference threshold.

In some embodiments, the two sides of the fixing member 101 may be provided with the indicator light, respectively. The user may determine whether the clamping anomaly occurs based on a situation of the indicator light. For example, if the indicator lights on the two sides show different situations (e.g., the indicator light of one side shows the red light, the indicator light of the other side shows the green light, etc.), the user may determine the clamping anomaly.

In some embodiments, the processor may determine whether the clamping anomaly exists based on the spring force information collected at a plurality of consecutive time points. For example, the processor may determine that the clamping anomaly exists in response to determining that a difference between the spring force information collected at consecutive time points is greater than the second difference threshold.

The first difference threshold and the second difference threshold may be determined based on experience or historical data. For example, the difference between the spring force information collected by force sensors at different positions when the clamping anomaly occurs in the historical experimental data may be counted, and a statistical value (e.g., an average value or a minimum value, etc.) of the difference may be used as the first difference threshold value, and a difference between the spring force information collected at consecutive time points when the clamping anomaly occurs may be counted, and the statistical value (e.g., the average value or the minimum value, etc.) of the difference may be used as the second difference threshold.

In some embodiments, when the locking buckle 302 extends and retracts, whether the clamping anomaly exists in the clip pieces 102 may be determined based on the spring force information. When the locking buckle 302 extends and retracts, in an ideal condition, the state of the clip pieces does not change, and the spring force information does not change. If the spring force information changes, the clamping anomaly may include unstable clamping caused by fatigue of a mechanical component (e.g., loosening of one side of the clip pieces caused by repeated, etc.).

By analyzing and determining the clamping anomaly, the clamping situation can be known in time, and accidents can be avoided.

In some embodiments, the processor may be further configured to: automatically record a clamping start time point and a clamping end time point of the hemostatic clip based on the spring force information.

For example, the processor may use a time point when the spring force information is greater than the second preset threshold (or a time point when the green light of the indicator light is on) as the clamping start time point of the hemostatic clip; a time point when the spring force information is reduced to be less than the second preset threshold (i.e., a time point when the green light of the indicator light is finally off) as the clamping end time point.

In some embodiments, the processor may automatically collect and record, based on the spring force information, a total duration for which a cumulative clamping force of the hemostatic clip satisfies a preset condition during each clamping process. The preset condition may be that the clamping force is greater than or equal to the second preset threshold and less than the first preset threshold. The first preset threshold and the second preset threshold may be determined according to the application scenario.

In some embodiments, a clamping duration when the clamping anomaly occurs is not counted in the total duration, thereby making the total duration more accurate.

The clamping duration of the hemostatic clip is recorded, such that the user accurately and reasonably counts the clamping duration of the clamping force, which avoids affecting the patient's physical function caused by accidental inaccuracy of the clamping duration, etc.

In some embodiments, the hemostatic clip assembly may further include a clamping sensor. The clamping sensor may be configured to collecting sensing information from the human body. The sensing information may include a myoelectric signal of a body tissue, etc. The clamping sensor may be provided on ends of the clip pieces 102 close to the target position.

The clamping sensor may send the collected myoelectric signal to a remote processing device. The remote processing device may evaluate a compression risk value corresponding to the clamping force based on the sensing information; and determine a clamping force adjustment based on the compression risk value.

The remote processing device may be a remote server, such as a computer, etc. The compression risk value refers to a risk value of causing compression to the target lesion or bleeding tissue in the human body.

In some embodiments, the remote processing device may determine the compression risk value based on the sensing information, a tissue type, and the clamping force through a compression risk model.

The tissue type may include a type of a clamped human tissue, organ, blood vessel, etc. The tissue type may be obtained through the user terminal.

The compression risk model may be configured to determine the compression risk value. The compression risk model may be a machine learning model, e.g., a neural networks (NN) model, a deep neural networks (DNN) model, etc.

In some embodiments, an input of the compression risk model may include the sensing information, the tissue type, and the clamping force; and output of the compression risk model may include the compression risk value.

In some embodiments, the compression risk model may be obtained by training based on a large number of first training samples and training labels corresponding to the training samples. The training samples may include sample sensing information, a sample tissue type, and a sample clamping force. The training labels may include sample compression risk values corresponding to the training samples, which may be expressed as a value in an interval [0, 1].

The training samples and the training labels may be obtained from historical or experimental data. For example, in the historical experiments, a plurality of experimental groups are set, each of the experimental groups sets a different tissue type and a different clamping force, subsequent sensing information is monitored under the different experimental groups, and the sensing information, the tissue type and the clamping force of each experimental group are used as a set of training samples. Different degrees of damage to the subsequently clamped tissue are manually evaluated and expressed as values in the interval [0, 1], and used as the training labels. Where 0 indicates that no damage is caused.

In some embodiments, a process of training the compression risk model may include: obtaining a training dataset, the training dataset including the plurality of training samples and the training labels corresponding to each of the training samples; performing a plurality of iterations, the at least one of iterations including: selecting one or more training samples from the training dataset and inputting the one or more training samples into the compression risk model to obtain model prediction outputs corresponding to the one or more of the samples; substituting the model prediction outputs and the training labels into a predefined formula of a loss function to calculate a value of the loss function; and inversely updating model parameters of the model based on the value of the loss function. An updating process may include gradient descent, etc. When an iteration end condition is satisfied, the iteration may be ended, and a trained compression risk model may be obtained.

In some embodiments, the input of the compression risk model may further include the application scenario and the total duration.

The training samples may further include the sample application scenario and the sample total duration.

The clamping force adjustment refers to a reduction in the clamping force. In some embodiments, the clamping force adjustment may be positively correlated with the compression risk value. When the compression risk value is greater than a preset risk threshold, the hemostatic clip may be released and the user may view an actual compression of the target lesion or bleeding tissue.

The clamping force and the compression risk value are quantified through the compression risk model, which facilitates the user to intuitively understand the clamping situation, and makes it easy to control the clamping effect of the hemostatic clip to avoid damaging the human body. Meanwhile, the compression risk value is evaluated through the compression risk model, which improves the accuracy of the evaluation, and improves the adjustment accuracy of the clamping force.

Some embodiments of the present disclosure provide a hemostatic clip. In some embodiments, the hemostatic clip may include a handle assembly and a hemostatic clip assembly. The handle assembly may be configured to drive the pulling device 4 of the hemostatic clip assembly to reciprocate.

The handle assembly is an assembly used to operate the movement of the pulling device 4. In some embodiments, the handle assembly may include an outer tube 10 and the drawstring 11, as shown in FIG. 6.

The outer tube 10 is a tube for the drawstring 11 to pass through. In some embodiments, the outer tube 10 may be a tube with relatively good flexibility, such as a spring tube, etc.

The drawstring 11 refers to a component for pulling the pulling device 4 to move. In some embodiments, one end of the connection shaft 9 may be connected with the sleeve 3, and the other end of the connection shaft 9 may be connected with the outer tube 10, and the drawstring 11 may pass through the outer tube 10 to be connected with the pulling device 4. A handle may be disposed on a proximal end of the drawstring 11, and the pulling device 4 may be controlled to reciprocate through the handle.

Figure 15:
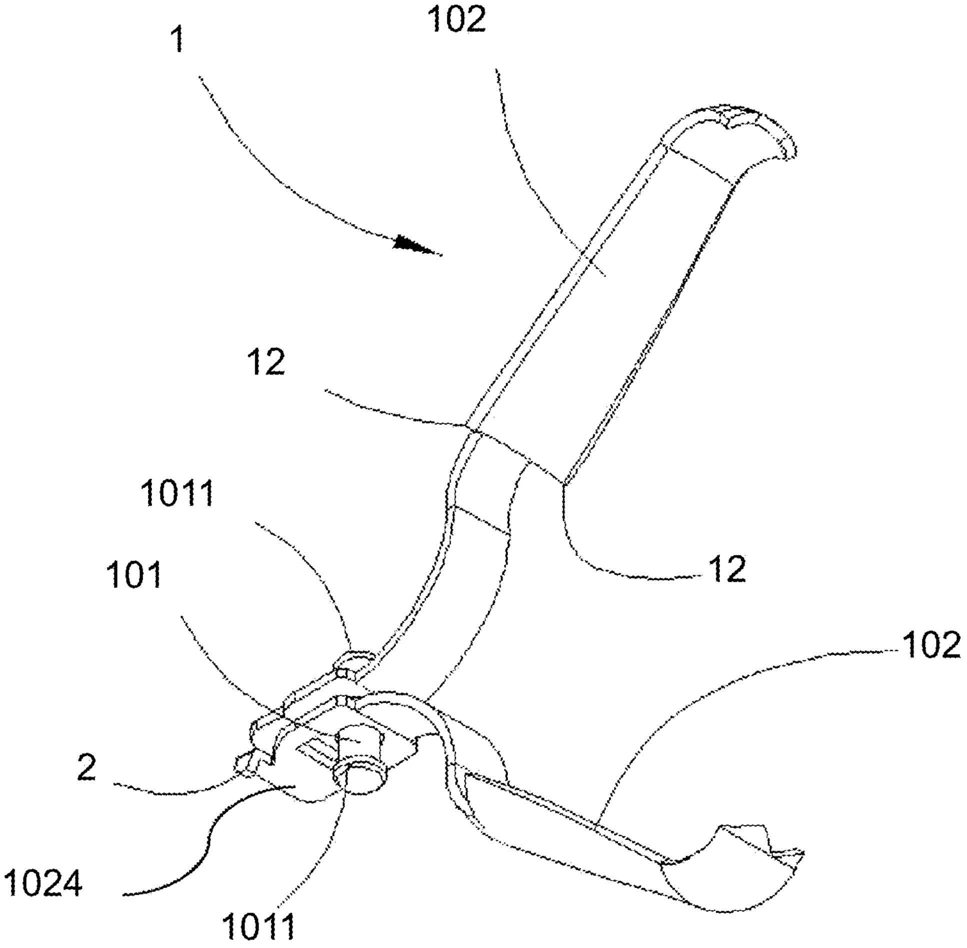
FIG. 15 is a three-dimensional schematic diagram illustrating two-piece forceps according to some embodiments of the present disclosure.
Figure 16:
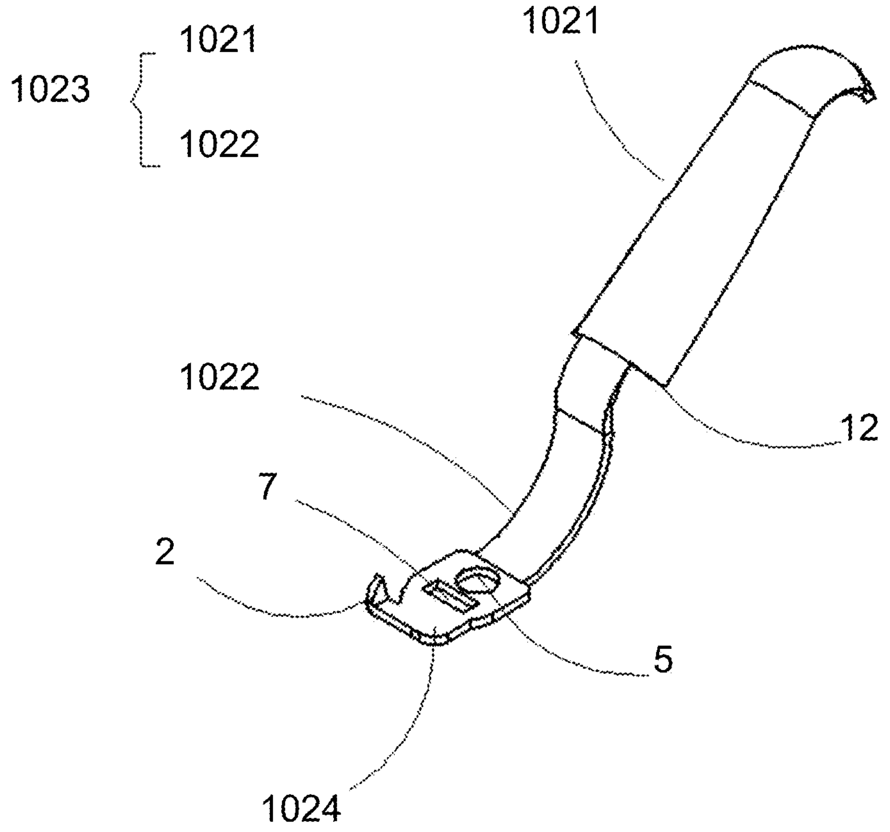
FIG. 16 is a three-dimensional schematic diagram illustrating a clip piece according to some embodiments of the present disclosure.

FIG. 15 is a three-dimensional schematic diagram illustrating two-piece forceps according to some embodiments of the present disclosure. FIG. 16 is a three-dimensional schematic diagram illustrating a clip piece according to some embodiments of the present disclosure.

Some embodiments of the present disclosure provide two-piece forceps. In some embodiments, as shown in FIG. 15 and FIG. 16, the two-piece forceps 1 may include the fixing member 101 and the two clip pieces 102 connected through the fixing member 101 and arranged opposite to each other. Each of the two clip pieces 102 may include a clip arm section 1023 and a clip tail section 1024 which extend from a distal end to a proximal end. The clip arm section 1023 may include a first clip section 1021 close to the distal end and a second clip section 1022 close to the proximal end, and the fixing member 101 may connect ends of the two clip tail sections 1024 close to the second clip sections 1022. One end of the clip tail section 1024 away from the second clip section 1022 may be provided with the first locking mechanism 2. The clip tail section 1024 may further include the second locking mechanism 7 provided between the fixing member 101 and the first locking mechanism 2. One end of the pulling device 4 of the hemostatic clip may be detachably connected with the two-piece forceps 1 through the second locking mechanism 7. In a natural state, ends of the two clip tail sections 1024 of the two clip pieces 102 away from the second clip sections 1022 may be disconnected, and an opening may be formed at the distal ends of the two first clip sections 1021 of the two clip pieces 102.

The clip arm section 1023 refers to a distal portion of the clip piece 102. In some embodiments, the clip arm section 1023 may include the first clip section 1021 disposed at the distal end and the second clip section 1022 disposed at the proximal end. In some embodiments, the two first clip sections 1021 may be close to each other to clamp the human tissue for compression hemostasis.

The clip tail section 1024 refers to a proximal portion of the clip piece 102.

The clip tail section 1024 and the first clip section 1021 may be open in a natural state. An unnatural state of the clip tail section 1024 is a state limited by the cooperation of the pulling device with the second locking mechanisms 7, and an unnatural state of the first clip section 1021 is a state in which the clip pieces 102 retract into the sleeve 3 to be constrained by an inner diameter of the sleeve 3.

Figure 17:
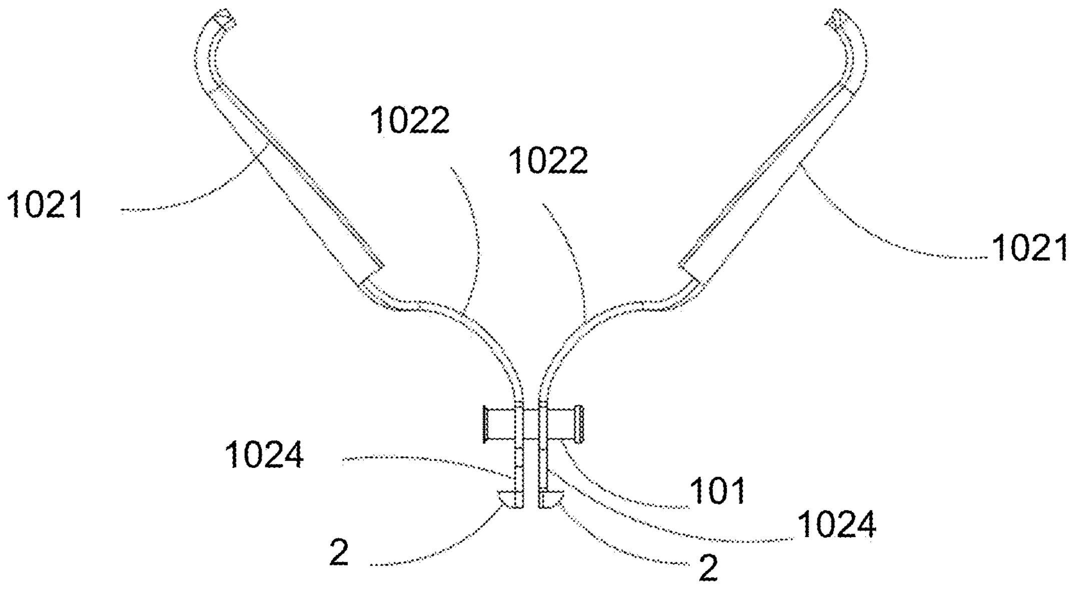
FIG. 17 is a schematic diagram illustrating a main view of two-piece forceps according to some embodiments of the present disclosure.

FIG. 17 is a schematic diagram illustrating a main view of two-piece forceps according to some embodiments of the present disclosure.

In some embodiments, the second clip sections 1022 may be curved, the two clip pieces 102 may be arranged side by side, and backs of curved portions the second clip sections 1022 may face each other. When the backs of the curved portions the two second clip sections 1022 fit, taking a closing process of the two-piece forceps 1 as an example, connection points of the backs of the curved portions of the two second clip sections 1022 gradually move toward the first clip sections 1021 due to the design of curved features of the second clip sections 1022 and the lever principle, and the two clip tail sections 1024 open outwardly in a free state. In the process of the two clip tail sections 1024 opening outwardly, the two first clip sections 1021 are gradually close to each other such that the two-piece forceps 1 are in a closed state. For example, the second clip sections 1022 may be approximately C-shaped (as shown in FIG. 17).

In some embodiments, the two clip pieces 102 may be independent of each other. The clip pieces 102 may be provided with the clip tail sections 1024, and the first locking mechanism 2, the second locking mechanism 7, and the fixing member 101 may be provided on each of the clip tail section 1024, which provides a high degree of functional integration without additional fitting structure. The second locking mechanism 7 may be disposed between the fixing member 101 and the first locking mechanism 2. When the pulling device is connected with the second locking mechanisms 7, the clip tail sections 1024 are always in the closed state, and the first locking mechanisms 2 cannot be activated. When the pulling device is disconnected from the second locking mechanisms 7, the first locking mechanisms 2 are activated, such that the timing of locking can be accurately controlled, and the sequence of the disconnection of the pulling device and the locking of the sleeve 3 and the clip pieces 102 can be controlled without the mechanical structure design or special selection of materials, which reduces the production cost.

More descriptions regarding the two-piece forceps 1 and the components thereof may be found in FIGS. 1-14 and the related descriptions thereof.

In some embodiments, the two clip pieces 102 may have the same structure and may be symmetrically arranged. Each of the two clip pieces 102 may include the clip arm section 1023 and the clip tail section 1024 extending from the distal end to the proximal end. The clip arm section 1023 may include the first clip section close to the distal end 1021 and the second clip section 1022 close to the proximal end. The fixing member 101 may connect ends of the two clip tail sections 1024 close to the second clip sections 1022.

In some embodiments, as shown in FIG. 15 and FIG. 16, the fixing member 101 may be a pin shaft, and one end of the clip tail section 1024 close to the second clip section 1022 may be provided with the shaft hole 5 for the pin shaft to pass through.

More descriptions regarding the pin shaft and the shaft hole 5 may be found in FIG. 2 and the related descriptions thereof.

In some embodiments, by providing the fixing member 101, the two clip pieces 102 can be prevented from running laterally within the sleeve 3, such that the two clip pieces 102 can move more stably in the axial direction, and the force exerted on the forceps by the operator can be relatively stable.

The first locking mechanism 2 refers to a component that is used to lock a clamping state of the clip pieces 102. In some embodiments, the first locking mechanism 2 may be provided at an end of the clip tail section 1024 away from the second clip section 1022. In some embodiments, the first locking mechanisms 2 may realize clamping and locking of the two clip pieces 102 by the second clip sections 1022 opening to cooperate with the sleeve 3.

Figure 18:
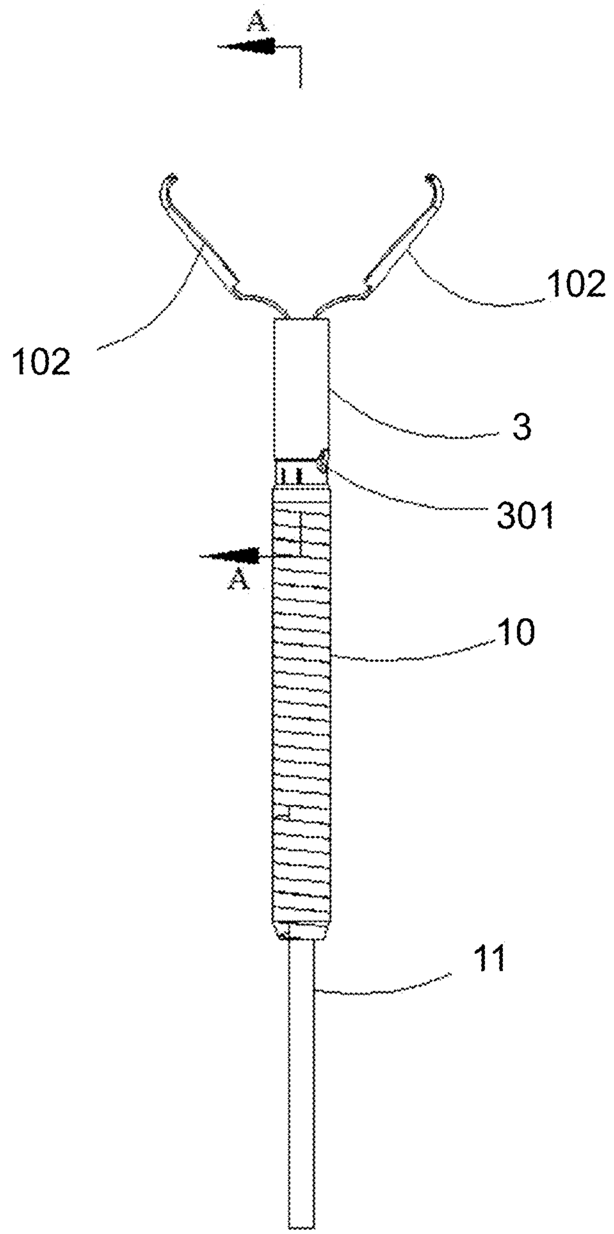
FIG. 18 is a schematic diagram illustrating a main view of a hemostatic clip in an open state according to some embodiments of the present disclosure.

FIG. 18 is a schematic diagram illustrating a main view of a hemostatic clip in an open state according to some embodiments of the present disclosure.

In some embodiments, as shown in FIG. 17 and FIG. 18, the first locking mechanisms 2 may be hooks that cooperate with the sleeve 3 of the hemostatic clip.

In some embodiments, when the two clip tail sections 1024 are open relative to each other or when the first clip sections 1021 are closed relative to each other, the hooks may cooperate with a slot in the sleeve 3 to secure the two-piece forceps 1 in the sleeve 3. More descriptions regarding the hooks and the sleeve may be found in FIGS. 2-9 and the related descriptions thereof.

In some embodiments, as shown in FIG. 16, the second locking mechanisms 7 of the forceps may be matching holes, and an edge of one end of each of the matching holes away from the second clip section 1022 may be a straight line.

In some embodiments, the edge of the one end of each of the matching holes away from the second clip section 1022 may be a straight edge, which can increase a matching contact surface of the pulling device 4 with the matching holes, thereby ensuring the stability of the pulling device 4 during pulling.

When the pulling device 4 is disconnected from the matching holes, friction is generated between the pulling device 4 and the edges of the matching holes to prevent the pulling device 4 from disconnecting from the matching holes. In some embodiments, a rounded transition may be set between an inner wall of an end of each of the matching holes away from the second clip section 1022 and an outer side of the clip tail section 1024, so as to reduce the friction generated between the pulling device 4 and the edges of the matching holes, and make the disconnection of the pulling device 4 smoother.

More descriptions regarding the matching holes may be found in FIGS. 1-15 and the related descriptions thereof.

Figure 19:
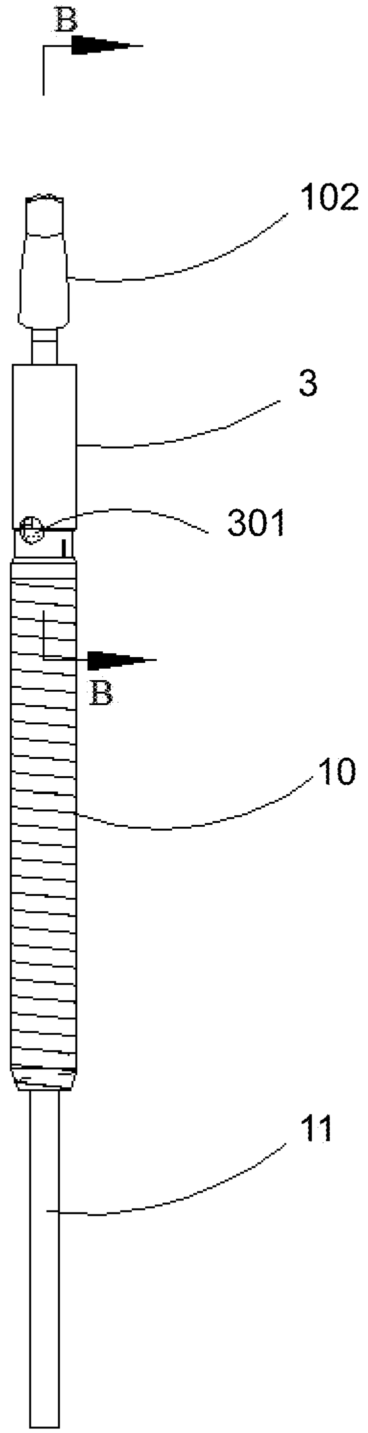
FIG. 19 is schematic diagram illustrating a right view of FIG. 18 according to some embodiments of the present disclosure.

FIG. 19 is schematic diagram illustrating a right view of FIG. 18 according to some embodiments of the present disclosure.

Figure 20:
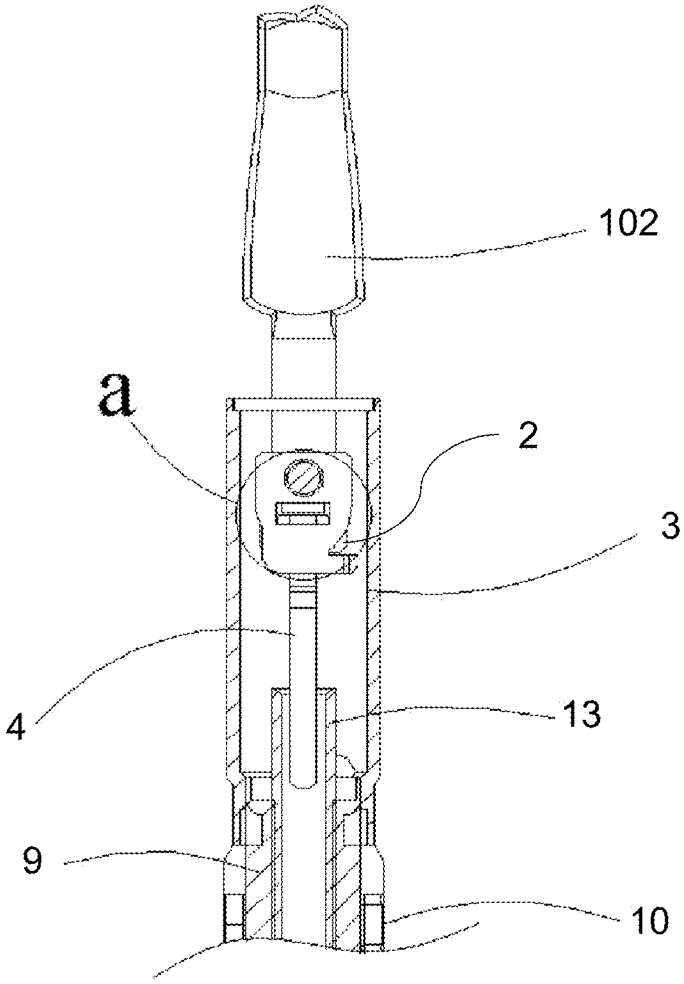
FIG. 20 is a schematic diagram illustrating an A-A direction sectional view of FIG. 18 according to some embodiments of the present disclosure.

FIG. 20 is a schematic diagram illustrating an A-A direction sectional view of FIG. 18 according to some embodiments of the present disclosure.

In some embodiments, as shown in FIGS. 18-20, a hemostatic clip may include the sleeve 3, the pulling device 4, and the two-piece forceps 1. The two-piece forceps 1 may be connected with the pulling device 4. The two-piece forceps 1 and the pulling device 4 may be at least partially located within the sleeve 3. The two-piece forceps 1 may move toward a proximal end under an action of the pulling device 4, and the sleeve 3 may make the two-piece forceps 1 in a closed state. In response to the pulling device 4 moving further toward the proximal end, the pulling device 4 may be disconnected from the 1 two-piece forceps, and the sleeve 3 may cooperate with the first locking mechanisms 2.

More descriptions regarding the two-piece forceps 1 may be found in FIGS. 15-17 and the related descriptions thereof. More descriptions regarding the pulling device of the sleeve may be found in FIGS. 1-15 and the related descriptions thereof.

In some embodiments, when the pulling device 4 pulls the two-piece forceps 1 to move toward the proximal end, the second clip sections 1022 of the two-piece forceps 1 may enter the sleeve 3, and under the constraint of a diameter size of the sleeve 3, the first locking mechanisms 2 on the two clip tail sections 1024 may be away from each other, the two first clip sections 1021 may be close to each other, and the two-piece forceps 1 may be in a closed clamping state (shown in FIG. 7). When the pulling device 4 continues to move toward the proximal end, the pulling device 4 may be disconnected from the second locking mechanism 7. When the pulling device 4 is disconnected from the two-piece forceps, the clip tail sections 1024 may lose a compression force, the two first locking mechanisms 2 may open freely, and the first locking mechanisms 2 may obediently clamp on the sleeve 3 and lock (as shown in FIG. 9).

Figure 21:
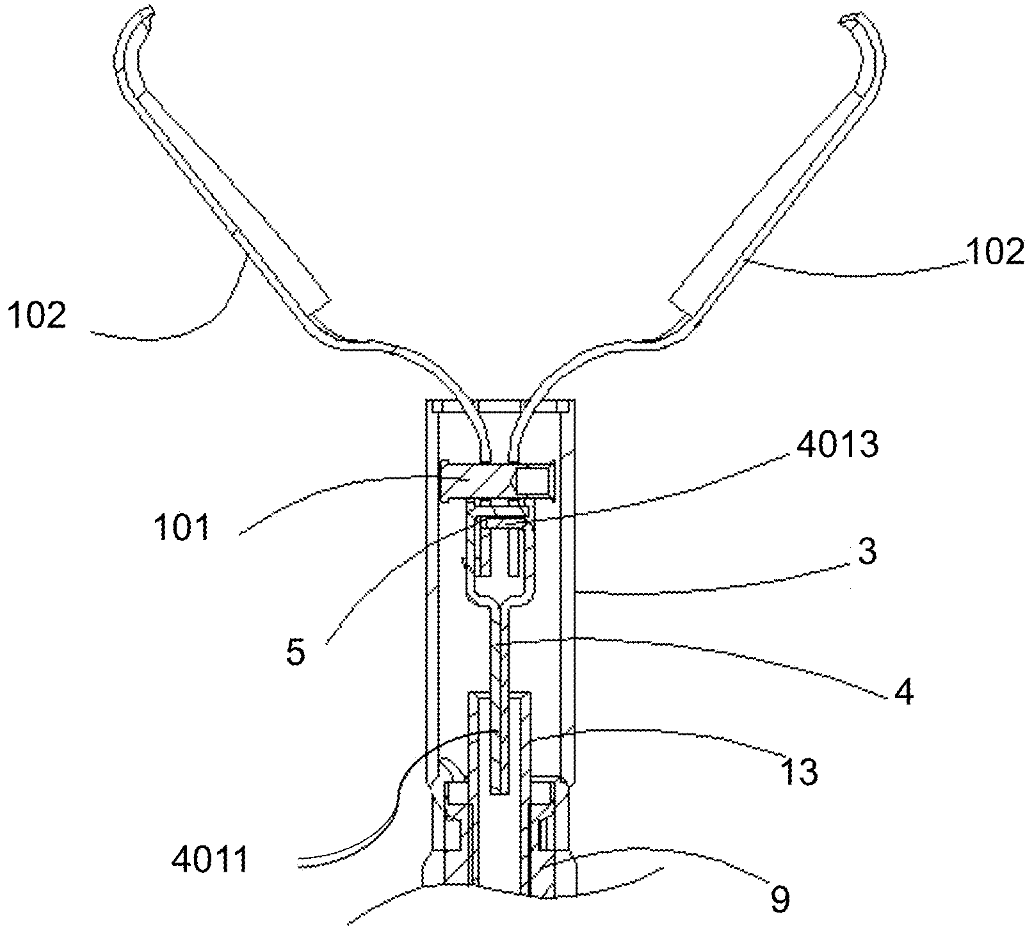
FIG. 21 is a schematic diagram illustrating an enlargement at a in FIG. 20 according to some embodiments of the present disclosure.
Figure 22:
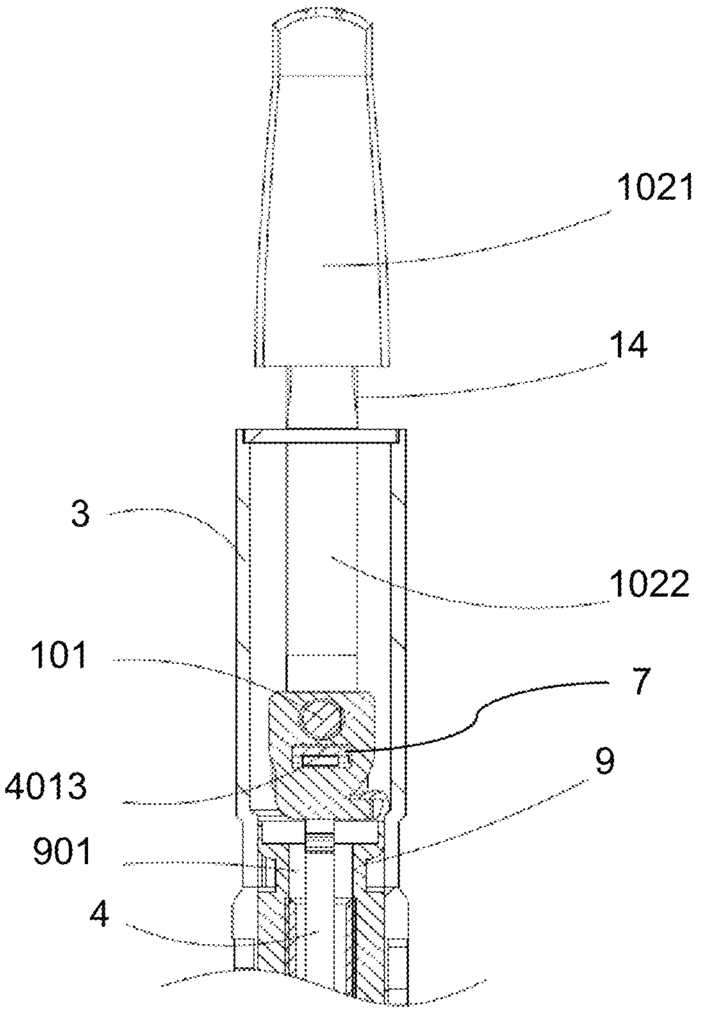
FIG. 22 is a schematic diagram illustrating a B-B direction sectional view of FIG. 19 according to some embodiments of the present disclosure.
Figure 23:
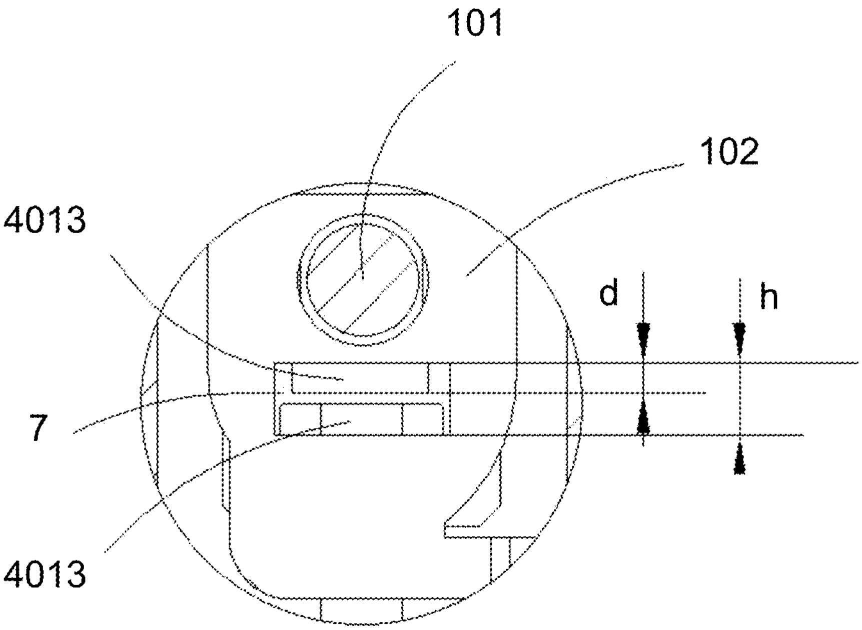
FIG. 23 is a schematic diagram illustrating an A-A direction sectional view of a hemostatic clamp in a view of FIG. 18 when two-piece forceps are initially closed according to some embodiments of the present disclosure.

FIG. 21 is a schematic diagram illustrating an enlargement at a in FIG. 20 according to some embodiments of the present disclosure. FIG. 22 is a schematic diagram illustrating a B-B direction sectional view of FIG. 19 according to some embodiments of the present disclosure. FIG. 23 is a schematic diagram illustrating an A-A direction sectional view of a hemostatic clamp in a view of FIG. 18 when two-piece forceps are initially closed according to some embodiments of the present disclosure.

In some embodiments, as shown in FIGS. 21-23, the pulling device 4 may include a rod portion 4011 and a connection portion which are connected with each other. The connection portion may be connected with the second locking mechanisms 7. The connection portion is capable of deforming and disconnecting from the second locking mechanisms 7 under a tensile force.

When the pulling device 4 is connected with the second locking mechanisms 7, the pulling device 4 may pull the two clip tail sections 1024 to be close to each other. When the pulling device 4 pushes the two-piece forceps 1 to move toward a distal end, the first clip sections 1021 may move to the outside of the sleeve 3, and the two first clip sections 1021 may open freely (as shown in FIG. 23).

In some embodiments, the connection portion may include baffle plates 4012 provided on two sides of the two clip tail sections 1024 and insert plates 4013 cooperating with the second locking mechanisms 7. The insert plates 4013 may be inserted into the second locking mechanisms 7 to make the two clip tail sections 1024 closed.

In some embodiments, the two insert plates 4013 may be arranged in at least one of a parallel arrangement, a V-shaped arrangement, a herringbone arrangement, or a figure-of-eight arrangement. More descriptions regarding the arrangement of the insert plates 4013 may be found in FIG. 3 and the related descriptions thereof.

In some embodiments, as shown in FIG. 21, the size of each of matching holes cannot be too large. If the height h of each of the matching holes is too large, a gap may be formed between the insert plate 4013 and an inner side of the matching hole, and the two-piece forceps 1 cannot respond to the action of the pulling device 4 in time when the pulling device 4 is pushed or pulled. When two mutually stacked insert plates 4013 fit the matching holes, the height h of each of the matching holes may be slightly greater than a sum of the thicknesses d of the two insert plates 4013, so as to allow the two insert plates 4013 to fit the inner sides of the matching holes.

Figure 24:
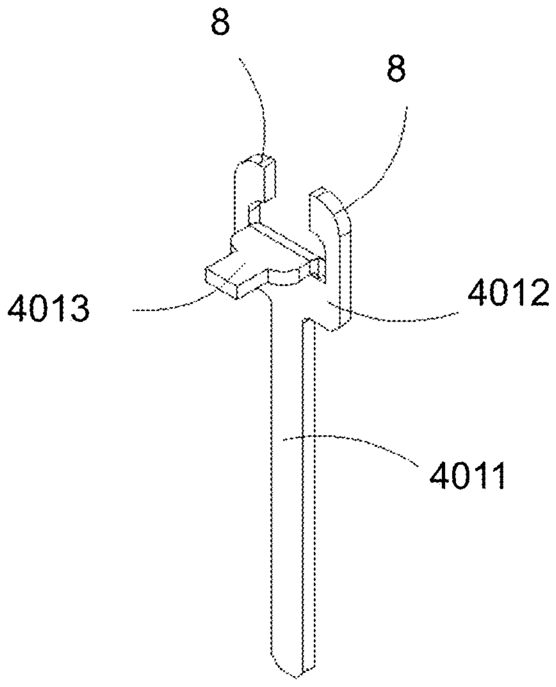
FIG. 24 is a schematic structural diagram illustrating a pulling plate according to some embodiments of the present disclosure.

FIG. 24 is a schematic structural diagram illustrating a pulling plate according to some embodiments of the present disclosure.

Figure 25:
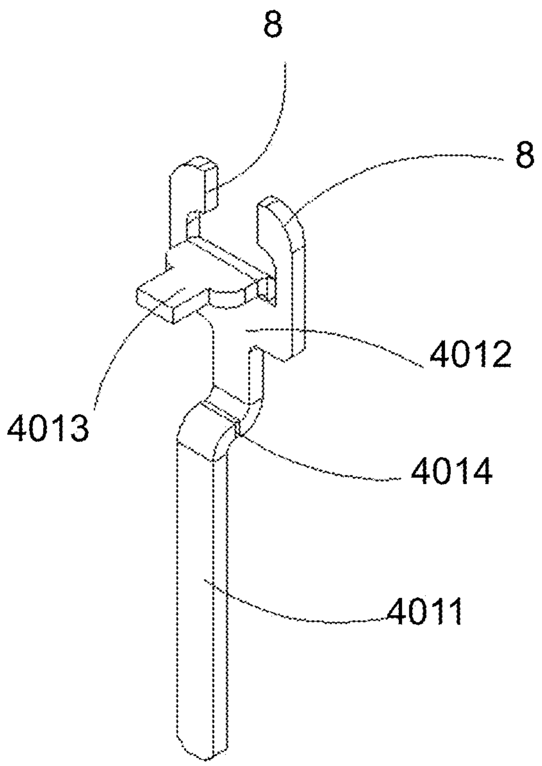
FIG. 25 is a schematic structural diagram illustrating a pulling plate according to some embodiments of the present disclosure.

FIG. 25 is a schematic structural diagram illustrating a pulling plate according to some embodiments of the present disclosure.

Figure 26:
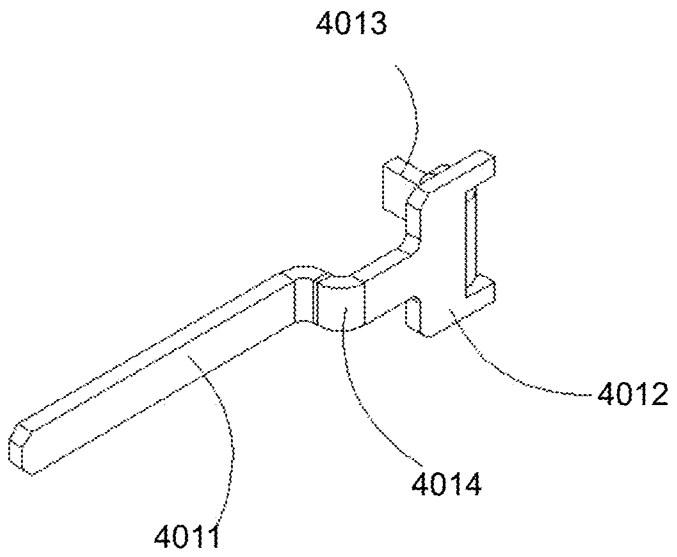
FIG. 26 is a schematic structural diagram illustrating a pulling plate according to some embodiments of the present disclosure.

FIG. 26 is a schematic structural diagram illustrating a pulling plate according to some embodiments of the present disclosure.

In some embodiments, as shown in FIGS. 24-26, the pulling device 4 may include two pulling plates 401 provided on two sides of the two clip tail sections 1024. Each of the two pulling plates 401 may include the rod portion 4011, the baffle plate 4012, and the insert plate 4013. Arrangement directions of the two pulling plates 401 may be the same as arrangement directions of the two clip pieces 102.

The baffle plates 4012 may be disposed on the two sides of the two clip tail sections 1024. The two clip tail sections 1024 may be provided with matching holes which are arranged opposite to each other, and the insert plates 4013 may cooperate with the matching holes. The two baffle plates 4012 may clamp the two clip tail sections 1024 to make the two clip tail sections 1024 close to each other. The two clip tail sections 1024 fit when the insert plates 4013 are inserted into the matching holes. The insert plates 4013 may be deformed and disconnected from the matching holes by a tensile force of the pulling device 4, so as to make the two clip tail sections 1024 in a free state.

In some embodiments, as shown in FIG. 24 and FIG. 25, the connection portion of the hemostatic clip may further include the limiting plate 8 extending toward the fixing member 101. The limiting plate 8 may be provided with an opening and the opening may face the fixing member 101. The fixing member 101 may be in clearance fitting with the limiting plate 8.

The limiting plate 8 may be disposed on two sides of the fixing member 101, respectively, which allows symmetry axes of the pulling device 4 and the two-piece forceps 1 to be in the same straight line, and prevents tilting of the pulling device 4. More descriptions regarding the limiting plate may be found in FIG. 3 and the related descriptions thereof.

More descriptions regarding the pulling device may be found in FIGS. 1-15 and the related descriptions thereof.

It should be understood that terms such as "center," "vertical," "horizontal," "inner," "outer," "axial," etc. indicate an orientation or positional relationship based only on the orientation or positional relationship shown in the accompanying drawings, and are used only for the purpose of facilitating the description of the present disclosure and simplifying the description and are not intended to indicate or imply that the device or element referred to must have a particular orientation, be constructed and operated in a particular orientation, and therefore cannot be construed as a limitation of the present disclosure.

In addition, the terms "first," "second," etc. are used for descriptive purposes only and are not to be understood as indicating or implying relative importance.

In addition, certain features, structures, or characteristics of one or more embodiments of the present disclosure may be suitably combined.

In some embodiments, numbers describing the number of ingredients and attributes are used. It should be understood that such numbers used for the description of the embodiments use the modifier "about", "approximately", or "substantially" in some examples. Unless otherwise stated, "about", "approximately", or "substantially" indicates that the number is allowed to vary by ±20%. Correspondingly, in some embodiments, the numerical parameters used in the description and claims are approximate values, and the approximate values may be changed according to the required features of individual embodiments. In some embodiments, the numerical parameters should consider the prescribed effective digits and adopt the method of general digit retention. Although the numerical ranges and parameters used to confirm the breadth of the range in some embodiments of the present disclosure are approximate values, in specific embodiments, settings of such numerical values are as accurate as possible within a feasible range.

For each patent, patent application, patent application publication, or other materials cited in the present disclosure, such as articles, books, specifications, publications, documents, or the like, the entire contents of which are hereby incorporated into the present disclosure as a reference. The application history documents that are inconsistent or conflict with the content of the present disclosure are excluded, and the documents that restrict the broadest scope of the claims of the present disclosure (currently or later attached to the present disclosure) are also excluded. It should be noted that if there is any inconsistency or conflict between the description, definition, and/or use of terms in the auxiliary materials of the present disclosure and the content of the present disclosure, the description, definition, and/or use of terms in the present disclosure is subject to the present disclosure.

What is claimed is:

1. A hemostatic clip assembly, comprising a sleeve, two-piece forceps, and a pulling device connected with the two-piece forceps, wherein the two-piece forceps and the pulling device are at least partially located within the sleeve;

the two-piece forceps include a fixing member and two clip pieces connected through the fixing member and arranged opposite to each other, each of the two clip pieces includes a first clip section close to a distal end and a second clip section close to a proximal end, the fixing member is provided through the second clip section;

the second clip section is provided with a first locking mechanism and a second locking mechanism, two second locking mechanisms being arranged opposite to each other, an end of the pulling device is detachably connected with the two-piece forceps through the second locking mechanisms and makes the two first locking mechanisms close to each other;

the sleeve is provided with a third locking mechanism, the two-piece forceps move toward the proximal end under an action of the pulling device when the pulling device is disconnected from the second locking mechanisms, the sleeve makes the two first clip sections of the two clip pieces close to each other;

the two first locking mechanisms move away from each other after the pulling device is disconnected from the second locking mechanisms, and the first locking mechanisms cooperate with the third locking mechanism in securing the two-piece forceps to the sleeve;

the pulling device includes a rod portion and a connection portion connected with each other, each of the second locking mechanisms is a matching hole, the connection portion includes an insert plate that cooperates with the matching hole, and the connection portion cooperates with the second locking mechanisms to connect the pulling device to the two-piece forceps;

the connection portion is capable of deforming and disconnecting from the second locking mechanisms under a tensile force toward the proximal end.

2. The hemostatic clip assembly of claim 1, wherein the fixing member is a pin shaft, and the second clip section is provided with a shaft hole for the pin shaft to pass through.

3. The hemostatic clip assembly of claim 2, wherein the third locking mechanism is a slot, and the first locking mechanism is a hook.

4. The hemostatic clip assembly of claim 2, wherein at least one axial end of the pin shaft is provided with a masking cap, wherein a diameter of the masking cap is greater than a diameter of the shaft hole.

5. The hemostatic clip assembly of claim 4, wherein when two ends of the pin shaft are provided with the masking cap, respectively, and telescopic springs are symmetrically distributed at inner sides of the masking caps at the two ends.

6. The hemostatic clip assembly of claim 5, wherein the fixing member is provided with at least one force sensor, and the at least one force sensor is configured to monitor and collect spring force information.

7. The hemostatic clip assembly of claim 6, wherein the at least one force sensor is provided between each of the telescopic springs and each of the masking caps.

8. The hemostatic clip assembly of claim 6, further comprising a processor, wherein the processor is configured to determine a clamping force of the two clip pieces of the two-piece forceps based on spring force information.

9. The hemostatic clip assembly of claim 1, wherein the pulling device includes two pulling plates provided on two sides of the two second clip sections, respectively, and each of the two pulling plates includes the rod portion and the connection portion.

10. The hemostatic clip assembly of claim 1, wherein two insert plates are arranged in two matching holes in at least one of a parallel opposite arrangement, a V-shaped arrangement, a herringbone arrangement, or a figure-of-eight arrangement.

11. The hemostatic clip assembly of claim 1, wherein the connection portion further includes a limiting plate extending toward the fixing member, the limiting plate is provided with an opening and the opening faces the fixing member, and the fixing member is clearance-fit with the limiting plate.

12. The hemostatic clip assembly of claim 11, wherein the limiting plate is provided between each of the clip tail sections and a flared end of the fixing member.

13. The hemostatic clip assembly of claim 1, further comprising a connection shaft axially limited to the proximal end of the sleeve, the connection shaft is provided with a central shaft for the pulling device to pass through, and the pulling device is capable of driving the connection shaft to move in a direction of the proximal end of the sleeve to disconnect the connection shaft from the sleeve.

14. The hemostatic clip assembly of claim 1, wherein the first locking mechanism is a hook that cooperates with the sleeve.

15. The hemostatic clip assembly of claim 14, wherein the sleeve is provided with a slot, and the hook is cooperated with the slot.

16. The hemostatic clip assembly of claim 1, wherein at least one set of magnetic sheets is provided on a distal inner wall of each of the two second clip sections, and magnetic forces of each set of the magnetic sheets is in opposite directions.

17. The hemostatic clip assembly of claim 1, wherein at least one set of magnetic sheets is provided on a proximal inner wall of each of the two second clip sections, and magnetic forces of each set of magnetic sheets is in opposite directions.

18. The hemostatic clip assembly of claim 1, wherein a center of curvature of one of the two second clip sections and a center of curvature of other of the two second clip sections are located on two sides of positions at which relative connection points of backs of curved portions of the two second clip sections are located, respectively.

19. The hemostatic clip assembly of claim 1, wherein a width of the first clip section is greater than a width of each of the second clip section to form a lateral boss at a proximal end of the first clip section.

* * * * *